(12) United States Patent
Fritzsche et al.

(10) Patent No.: US 7,695,643 B2
(45) Date of Patent: Apr. 13, 2010

(54) LONG WAVELENGTH SHIFTED BENZOTRIAZOLE UV-ABSORBERS AND THEIR USE

(75) Inventors: Katharina Fritzsche, Weil am Rhein (DE); Adalbert Braig, Binzen (DE); Markus Frey, Rheinfelden (CH); Walter Fischer, Reinach (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 288 days.

(21) Appl. No.: 11/795,543

(22) PCT Filed: Jan. 23, 2006

(86) PCT No.: PCT/EP2006/050354

§ 371 (c)(1),
(2), (4) Date: Jul. 18, 2007

(87) PCT Pub. No.: WO2006/082145

PCT Pub. Date: Aug. 10, 2006

(65) Prior Publication Data

US 2008/0157025 A1  Jul. 3, 2008

(30) Foreign Application Priority Data

Feb. 2, 2005  (EP)  ................... 05100703

(51) Int. Cl.
| | |
|---|---|
| *C09K 15/04* | (2006.01) |
| *C09K 15/32* | (2006.01) |
| *C09K 15/22* | (2006.01) |
| *C09K 15/00* | (2006.01) |
| *C09K 15/16* | (2006.01) |
| *C07D 487/00* | (2006.01) |
| *C07D 249/16* | (2006.01) |
| *C07D 249/20* | (2006.01) |
| *C07D 403/00* | (2006.01) |

(52) U.S. Cl. .................. 252/403; 252/399; 252/401; 252/404; 252/405; 548/256; 548/257; 548/259

(58) Field of Classification Search ................. 252/403; 548/256, 257, 259
See application file for complete search history.

(56) References Cited

U.S. PATENT DOCUMENTS 5,360,692 A * 11/1994 Kawabe et al. .............. 430/191
2004/0013619 A1   1/2004 Reinehr et al. ................ 424/59

FOREIGN PATENT DOCUMENTS

| EP | 0 717 313 | 6/1996 |
|---|---|---|
| GB | 2 346 369 | 8/2000 |
| WO | 02/28854 | 4/2002 |

OTHER PUBLICATIONS

"Contributo allo studio degli aminoazo-, ossiazo- e idrazocomposti", Charrier, G., Gassetta Chimica Italiana, 52(I), pp. 261-277, 1922.*

* cited by examiner

*Primary Examiner*—Mark Eashoo
*Assistant Examiner*—Peter F Godenschwager
(74) *Attorney, Agent, or Firm*—Shiela A. Loggins

(57) ABSTRACT

The invention relates to novel benzotriazole UV-absorbers having a long wavelength shifted absorption spectrum with significant absorbance up to 410-420 nm. Further aspects of the invention are a process for their preparation, a UV stabilized composition containing the new UV-absorbers and the use of the new compounds as UV-light stabilizers for organic materials.

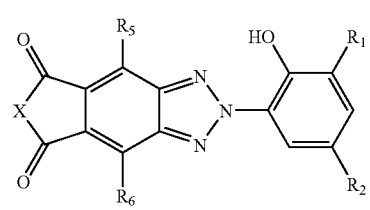

(I)

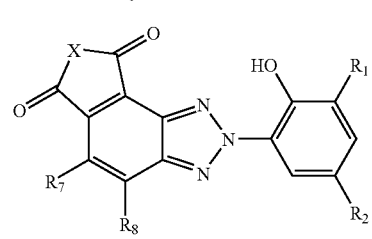

(II)

19 Claims, No Drawings

LONG WAVELENGTH SHIFTED BENZOTRIAZOLE UV-ABSORBERS AND THEIR USE

The instant invention relates to novel benzotriazole UV-absorbers having a long wavelength shifted absorption spectrum with significant absorbance up to 410-420 nm. Further aspects of the invention are a process for their preparation, a UV stabilized composition containing the new UV-absorbers and the use of the new compounds as UV-light stabilizers for organic materials.

Polymeric substrates containing aromatic moieties, such as for example adhesives or coating resins based on aromatic epoxides, aromatic polyesters or aromatic (poly-) isocyanates are highly sensitive to UV/VIS radiation up to wavelengths of approximately 410 to 420 nm.

The protection of such adhesive or coating layers with a UV absorbing layer on top is extremely difficult, since already very small amounts of radiation—even in the range of around 410 nm—penetrating the UV absorbing top coating are sufficient to cause delamination and peeling off of the protective coating.

Typical applications, in which long wavelength shifted UV absorbers are extremely useful, are automotive coatings, typically two coat metallic automotive coatings.

Today's automotive coatings have applied an anticorrosive cathodic electro coat directly on the steel plate. Due to the significantly red shifted light sensitivity of the cathodic resins (up to approximately 400-410 nm) it is not possible to protect the cathodic electro coat with conventional prior art UV-absorbers in the top coatings adequately.

In order to better protect such sensitive layers, attempts have been made to shift the UV absorption of benzotriazoles towards longer wavelengths. For example, U.S. Pat. No. 5,436,349 discloses benzotriazole UV-absorbers, which are substituted in the 5 position of the benzo ring by alkylsulfonyl groups. However, the absorption shift is not large enough to protect such highly sensitive materials.

U.S. Pat. No. 6,166,218 discloses, for example, benzotriazole UV-absorbers, which are substituted in the 5-position of the benzo ring with a $CF_3$ group, leading also to a slightly long wavelength shifted absorbance and to an enhanced photochemical stability. This absorption shift, however, is by far not large enough to protect materials with a photochemical sensitivity up to 410 nm.

Surprisingly it has now been found, that when the benzo ring of benzotriazole UV-absorbers is part of a phthalic acid anhydride or imide system a large shift of the absorption maximum of approximately 20-30 nm is observed, extending up to 420 nm. The compounds remain unexpectedly photochemically stable and show virtually no migration in typical coating applications.

One aspect of the invention is a compound of formulae (I) or (II)

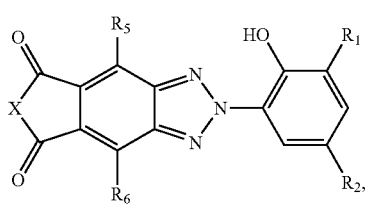

(I)

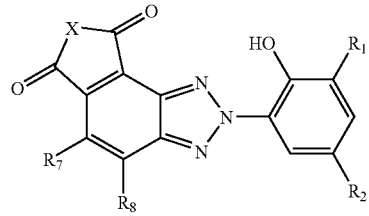

(II)

wherein $R_1$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $R_1$ is a group

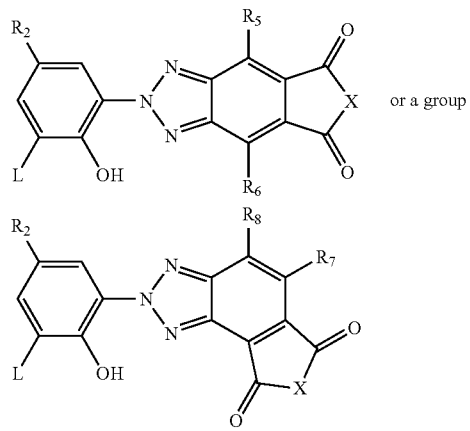

or a group wherein L is alkylene of 1 to 12 carbon atoms, alkylidene of 2 to 12 carbon atoms, benzylidene, p-xylylene or cycloalkylene of 5 to 7 carbon atoms;

$R_2$ is straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or said alkyl substituted by one or more —OH, —OCO—$R_{11}$, —O$R_{14}$, —NCO or —NH$_2$ groups or mixtures thereof, or said alkyl or said alkenyl interrupted by one or more —O—, —NH— or —NR$_{14}$— groups or mixtures thereof and which can be unsubstituted or substituted by one or more —OH, —OR$_{14}$ or —NH$_2$ groups or mixtures thereof; where $R_{11}$ is hydrogen, straight or branched chain $C_1$-$C_{18}$alkyl, $C_5$-$C_{12}$cycloalkyl, straight or branched chain $C_3$-$C_8$alkenyl, phenyl, naphthyl or $C_7$-$C_{15}$phenylalkyl; and $R_{14}$ is hydrogen, straight or branched chain alkyl of 1 to 24 carbon atoms; or $R_2$ is —OR$_{14}$, a group —C(O)—O—R$_{14}$, —C(O)—NHR$_{14}$ or —C(O)—NR$_{14}$R'$_{14}$ wherein R'$_{14}$ has the same meaning as $R_{14}$; or $R_2$ is —$SR_{13}$, —$NHR_{13}$ or —$N(R_{13})_2$; or $R_2$ is —$(CH_2)_m$—CO—$X_1$-$(Z)_p$-Y—$R_{15}$ wherein
  $X_1$ is —O— or —$N(R_{16})$—,
  Y is —O— or —$N(R_{17})$— or a direct bond,
  Z is $C_2$-$C_{12}$-alkylene, $C_4$-$C_{12}$alkylene interrupted by one to three nitrogen atoms, oxygen atoms or a mixture thereof, or is $C_3$-$C_{12}$alkylene, butenylene, butynylene, cyclohexylene or phenylene, each of which may be additionally substituted by a hydroxyl group;
  or a group

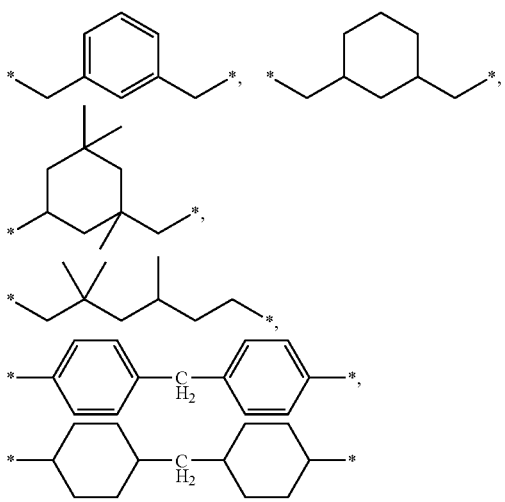

wherein * denotes a bond;
or when Y is a direct bond, Z can additionally also be a direct bond;
m is zero, 1 or 2,
p is 1, or p is also zero when X and Y are —$N(R_{16})$— and —$N(R_{17})$—, respectively,
$R_{15}$ is hydrogen, $C_1$-$C_{12}$alkyl, a group

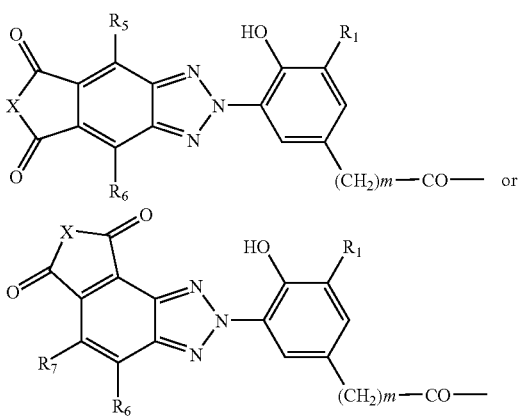

or a group —CO—$C(R_{18})$=$C(H)R_{19}$ or, when Y is —$N(R_{17})$—, forms together with $R_{17}$ a group —CO—CH=CH—CO— wherein $R_{18}$ is hydrogen or methyl, and $R_{19}$ is hydrogen, methyl or —CO—$X_1$—$R_{20}$, wherein $R_{20}$ is hydrogen, $C_1$-$C_{12}$alkyl or a group of formulae

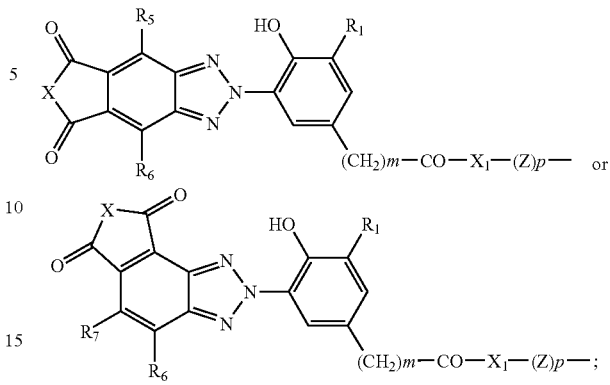

$R_5$, $R_6$, $R_7$ and $R_8$ are independently hydrogen, halogen, CN, $NO_2$ or $NH_2$;

$R_{13}$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, phenyl or naphthyl, which both may be substituted by one or two alkyl of 1 to 4 carbon atoms;

$R_{16}$ and $R_{17}$ independently of one another are hydrogen, $C_1$-$C_{12}$-alkyl, $C_3$-$C_{12}$-alkyl interrupted by 1 to 3 oxygen atoms, or is cyclohexyl or $C_7$-$C_{15}$phenylalkyl, and $R_{16}$ together with $R_{17}$ in the case where Z is ethylene, also forms ethylene;

X is O or NE, wherein $E_1$ is hydrogen, straight or branched chain $C_1$-$C_{24}$alkyl, straight or branched chain $C_2$-$C_{18}$alkenyl, $C_2$-$C_6$alkyinyl, $C_5$-$C_{12}$cycloalkyl, phenyl, naphthyl or $C_7$-$C_{15}$phenylalkyl; or said straight or branched chain $C_1$-$C_{24}$ alkyl, straight or branched chain $C_2$-$C_{24}$ alkenyl, $C_5$-$C_{12}$ cycloalkyl, $C_2$-$C_6$ alkinyl can be substituted by one or more —F, —OH, —$OR_{22}$, —$NH_2$, —$NHR_{22}$, —$N(R_{22})_2$, —$NHCOR_{23}$, —$NR_{22}COR_{23}$, —$OCOR_{24}$, —$COR_{25}$, —$SO_2R_{26}$, —PO$(R_{27})_n(R_{28})_{2-n}$, —Si$(R_{29})_n(R_{30})_{3-n}$, —Si$(R_{22})_3$, —$N^+(R_{22})_3$ $A^-$, —$S^+(R_{22})_2A^-$, -oxiranyl groups or mixtures thereof; said straight or branched chain $C_1$-$C_{24}$ alkyl, straight or branched chain unsubstituted or substituted $C_2$-$C_{24}$ alkenyl, $C_5$-$C_{12}$ cycloalkyl or $C_2$-$C_6$ alkinyl can also be interrupted by one or more —O—, —S—, —NH— or —$NR_{22}$— groups or combinations thereof;

said phenyl, naphthyl or $C_7$-$C_{15}$phenylalkyl can also be substituted by one or more -halogen, —CN, —$CF_3$, —$NO_2$, —$NHR_{22}$, —$N(R_{22})_2$, —$SO_2R_{26}$, —PO$(R_{27})_n(R_{28})_{2-n}$, —OH, —$OR_{22}$, —$COR_{25}$, —$R_{25}$;

wherein n is 0, 1 or 2;

$R_{22}$ is straight or branched chain $C_1$-$C_{18}$ alkyl, straight or branched chain $C_2$-$C_{18}$ alkenyl, $C_5$-$C_{10}$ cycloalkyl, phenyl or naphthyl, $C_7$-$C_{15}$ phenylalkyl, or two $R_{22}$ when attached to an N or Si atom can form together with the atom to which they are bonded a pyrrolidine, piperidine or morpholine ring;

$R_{23}$ is hydrogen, $OR_{22}$, $NHR_{22}$, $N(R_{22})_2$ or has the same meaning as $R_{22}$, $R_{24}$ is $OR_{22}$, $NHR_{22}$, $N(R_{22})_2$ or has the same meaning as $R_{22}$, $R_{25}$ is hydrogen, OH, $OR_{22}$, $NHR_{22}$ or $N(R_{22})_2$, O-glycidyl or has the same meaning as $R_{22}$, $R_{26}$ is OH, $OR_{22}$, $NHR_{22}$ or $N(R_{22})_2$, $R_{27}$ is $NH_2$, $NHR_{22}$ or $N(R_{22})_2$, $R_{28}$ is OH or $OR_{22}$, $R_{29}$ is Cl or $OR_{22}$, $R_{30}$ is straight or branched chain $C_1$-$C_{18}$ alkyl; or $E_1$ is a group

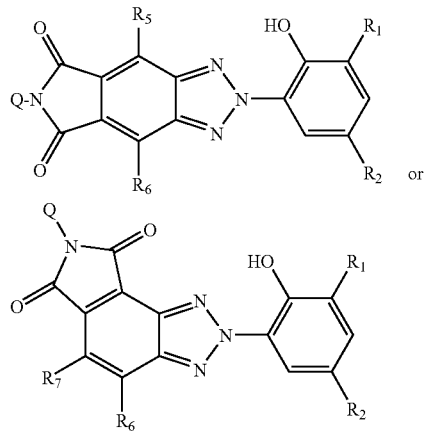

wherein $R_1$ to $R_8$ have the meanings as defined above and

Q is straight or branched $C_2$-$C_{12}$alkylene, $C_2$-$C_{12}$alkylene, which is interrupted by one or more —O—, NH or $NR_{14}$ atoms, $C_5$-$C_{10}$cycloalkylene, para-phenylene or a group

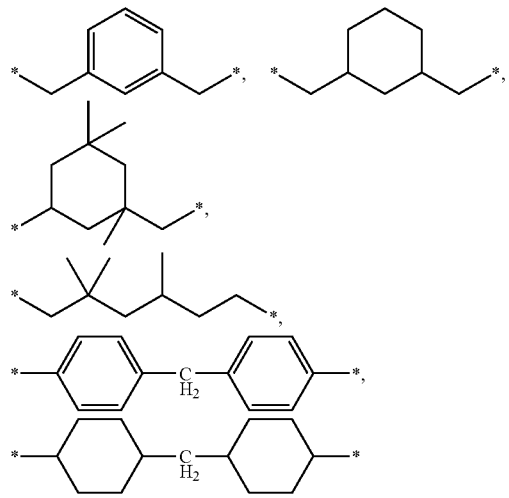

wherein * denotes a bond. Halogen is, for example, fluorine, chlorine, bromine or iodine. Chlorine is preferred.

When any of the substituents are straight or branched chain alkyl of 1 to 24 carbon atoms, such groups are, for example, methyl, ethyl, isopropyl, n-butyl, isobutyl, sec-butyl, tert-butyl, tert-amyl, 2-ethylhexyl, tert-octyl, lauryl, tert-dodecyl, tridecyl, n-hexadecyl, n-octadecyl or eicosyl.

When any of said substituents are straight or branched chain alkenyl of 2 to 18 carbon atoms, such groups are, for example, allyl, pentenyl, hexenyl, doceneyl or oleyl. Preference is given to alkenyl having from 3 to 16, especially from 3 to 12, for example from 2 to 6, carbon atoms.

When any of said substituents are cycloalkyl of 5 to 12 carbon atoms, such groups are, for example, cyclopentyl, cyclohexyl, cycloheptyl, cyclooctyl and cyclododecyl.

$C_1$-$C_4$alkyl-substituted $C_5$-$C_8$cycloalkyl is, for example, methylcyclopentyl, dimethylcyclopentyl, methylcyclohexyl, dimethylcyclohexyl, trimethylcyclohexyl or tert-butylcyclohexyl.

When any of said radicals are phenylalkyl of 7 to 15 carbon atoms, such groups are, for example, benzyl, phenethyl, α-methylbenzyl or α,α-dimethylbenzyl.

When phenyl is substituted by alkyl, this is, for example, tolyl and xylyl.

Alkyl substituted by one or more —O— groups and/or substituted by one or more —OH can, for example, be —$(OCH_2CH_2)_w$OH or —$(OCH_2CH_2)_wO(C_1$-$C_{24}$alkyl) where w is 1 to 12.

Alkyl interrupted by one or more —O— can be derived from ethyleneoxide units or from propyleneoxide units or from mixtures of both.

When alkyl is interrupted by —NH— or —$NR_{14}$— the radicals are derived in analogy to the above —O— interrupted radicals. Preferred are repeating units of ethylenediamine.

Examples are $CH_3$—O—$CH_2CH_2$—, $CH_3$—NH—$CH_2CH_2$—, $CH_3$—$N(CH_3)$—$CH_2$—, $CH_3$—O—$CH_2CH_2$—O—$CH_2CH_2$—, $CH_3$—(O—$CH_2CH_2$—)$_2$O—$CH_2CH_2$—, $CH_3$—(O—$CH_2CH_2$—)$_3$O—$CH_2CH_2$— or $CH_3$—(O—$CH_2CH_2$—)$_4$O—$CH_2CH_2$—.

Alkylene is, for example, ethylene, tetramethylene, hexamethylene, 2-methyl-1,4-tetramethylene, hexamethylene, octamethylene, decamethylene and dodecamethylene.

Cycloalkylene is, for example, cyclopentylene, cyclohexylene, cycloheptylene, cyclooctylene and cyclododecylene. Preference is given to cyclohexylene.

Alkylene interrupted by oxygen, NH or —$NR_{14}$— is, for example, —$CH_2CH_2$—O—$CH_2CH_2$—, —$CH_2CH_2$—NH—$CH_2CH_2$—, —$CH_2CH_2$—$N(CH_3)$—$CH_2CH_2$—, —$CH_2CH_2$—O—$CH_2CH_2$—O—$CH_2CH_2$—, —$CH_2CH_2$—(O—$CH_2CH_2$—)$_2$O—$CH_2CH_2$—, —$CH_2CH_2$—(O—$CH_2CH_2$—)$_3$O—$CH_2CH_2$—, —$CH_2CH_2$—(O—$CH_2CH_2$—)$_4$O—$CH_2CH_2$— or —$CH_2CH_2$—NH—$CH_2CH_2$—.

The radical Q is straight or branched $C_1$-$C_{12}$alkylene, $C_5$-$C_{10}$cycloalkylene, para-phenylene or a group

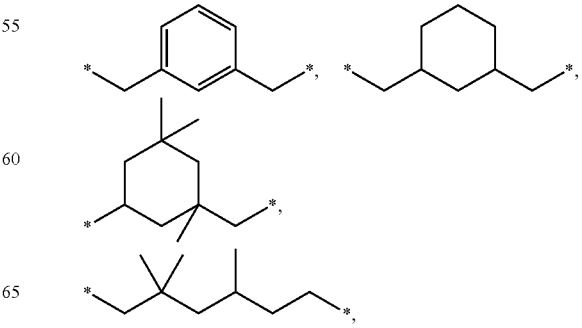

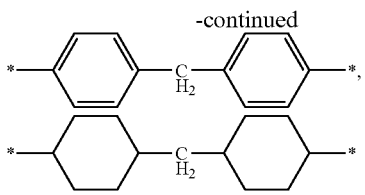

wherein * denotes a bond.

The radical can be derived from readily available diamines, for example, so called Jeffamines. Examples for diamines are Ethylenediamine, propylenediamine, 2-methyl-1,5-pentamethylendiamine, isophorondiamine or 1,2-diaminocyclohexane.

In analogy the radical Z can also be derived from the same available diamines or from the corresponding diols.

Typical Jeffamines are, for example D-2000

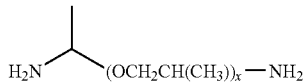

wherein x is 33.1 or ED-2003

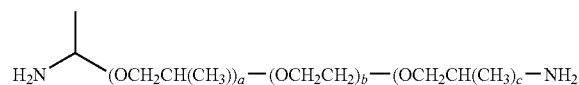

wherein a+c is 5 and b is 39.5.

Preference is given to a compound of formulae (I) or (II) wherein $R_1$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $R_1$ is a group

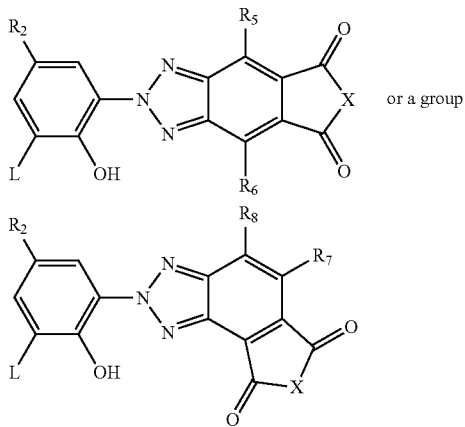 or a group wherein L is alkylene of 1 to 12 carbon atoms, alkylidene of 2 to 12 carbon atoms, benzylidene, p-xylylene or cycloalkylene of 5 to 7 carbon atoms;

$R_2$ is straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $R_2$ is —$(CH_2)_m$—CO—$X_1$-$(Z)_p$-Y—$R_{15}$ wherein
  $X_1$ is —O—,
  Y is —O— or a direct bond,
  Z is $C_2$-$C_{12}$-alkylene, $C_4$-$C_{12}$alkylene interrupted by one to three nitrogen atoms, oxygen atoms or a mixture thereof, or when Y is a direct bond, Z can additionally also be a direct bond;
  m is 2,
  p is 1,
  $R_{15}$ is hydrogen, $C_1$-$C_{12}$alkyl or a group

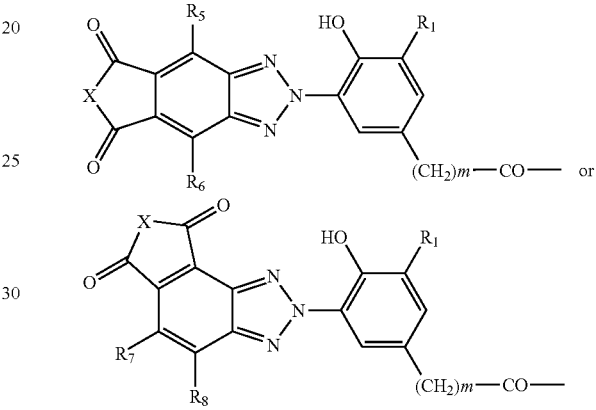

$R_5$, $R_6$, $R_7$ and $R_8$ are independently hydrogen, Cl or Br;

X is O or $NE_1$ wherein $E_1$ is hydrogen, straight or branched chain $C_1$-$C_{24}$alkyl, straight or branched chain $C_2$-$C_{18}$alkenyl, $C_2$-$C_6$alkyinyl, $C_5$-$C_{12}$cycloalkyl, phenyl, naphthyl or $C_7$-$C_{15}$phenylalkyl; or said straight or branched chain $C_1$-$C_{24}$ alkyl, straight or branched chain $C_2$-$C_{24}$ alkenyl, $C_5$-$C_{12}$ cycloalkyl, $C_2$-$C_6$ alkinyl can be substituted by one or more —F, —OH, —$OR_{22}$, —$NH_2$, —$NHR_{22}$, —$N(R_{22})_2$, —$NHCOR_{23}$, —$NR_{22}COR_{23}$, —$OCOR_{24}$, —$COR_{25}$, —$SO_2R_{26}$, —$PO(R_{27})_n(R_{28})_{2-n}$, —$Si(R_{29})_n(R_{30})_{3-n}$, —$Si(R_{22})_3$, —$N^+(R_{22})_3$ $A^-$, —$S^+(R_{22})_2A^-$, -oxiranyl groups or mixtures thereof; said straight or branched chain $C_1$-$C_{24}$ alkyl, straight or branched chain unsubstituted or substituted $C_2$-$C_{24}$ alkenyl, $C_5$-$C_{12}$ cycloalkyl or $C_2$-$C_6$ alkinyl can also be interrupted by one or more —O—, —S—, —NH— or —$NR_{22}$— groups or combinations thereof;

said phenyl, naphthyl or $C_7$-$C_{15}$phenylalkyl can also be substituted by one or more -halogen, —CN, —$CF_3$, —$NO_2$, —$NHR_{22}$, —$N(R_{22})_2$, —$SO_2R_{26}$, —$PO(R_{27})_n(R_{28})_{2-n}$, —OH, —$OR_{22}$, —$COR_{25}$, —$R_{25}$;

wherein n is 0, 1 or 2;

$R_{22}$ is straight or branched chain $C_1$-$C_{18}$ alkyl, straight or branched chain $C_2$-$C_{18}$ alkenyl, $C_5$-$C_{10}$ cycloalkyl, phenyl or naphthyl, $C_7$-$C_{15}$ phenylalkyl, or two $R_{22}$ when attached to an N or Si atom can form together with the atom to which they are bonded a pyrrolidine, piperidine or morpholine ring;

$R_{23}$ is hydrogen, $OR_{22}$, $NHR_{22}$, $N(R_{22})_2$ or has the same meaning as $R_{22}$, $R_{24}$ is $OR_{22}$, $NHR_{22}$, $N(R_{22})_2$ or has the same meaning as $R_{22}$, $R_{25}$ is hydrogen, OH, $OR_{22}$, $NHR_{22}$ or $N(R_{22})_2$, O-glycidyl or has the same meaning as $R_{22}$, $R_{26}$ is OH, $OR_{22}$, $NHR_{22}$ or $N(R_{22})_2$, $R_{27}$ is $NH_2$, $NHR_{22}$ or $N(R_{22})_2$, $R_{28}$ is OH or $OR_{22}$, $R_{29}$ is Cl or $OR_{22}$, $R_{30}$ is straight or branched chain $C_1$-$C_{18}$ alkyl; or $E_1$ is a group

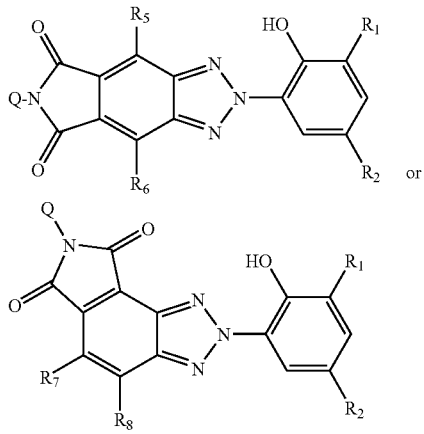

wherein $R_1$ to $R_8$ have the meanings as defined above and

Q is straight or branched $C_2$-$C_{12}$alkylene, $C_5$-$C_{10}$cycloalkylene or para-phenylene or a group.

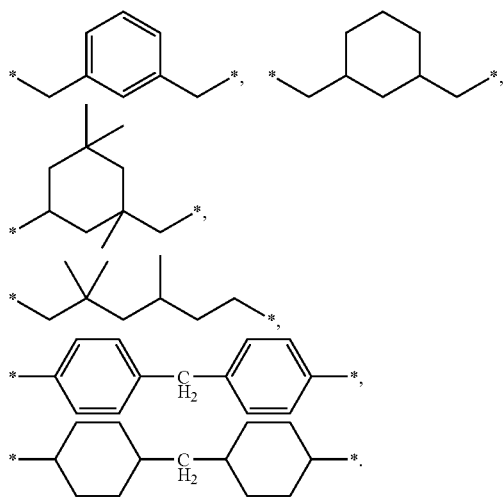

For example, in the compound of formula (I) or (II)

$R_1$ is hydrogen, straight or branched chain alkyl of 1 to 24 carbon atoms, straight or branched chain alkenyl of 2 to 18 carbon atoms, cycloalkyl of 5 to 12 carbon atoms, phenyla-lkyl of 7 to 15 carbon atoms, phenyl, or said phenyl or said phenylalkyl substituted on the phenyl ring by 1 to 4 alkyl of 1 to 4 carbon atoms $R_2$ is straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $R_2$ is —$(CH_2)_2$—CO—O-(Z)-O—$R_{15}$ wherein
Z is $C_2$-$C_{12}$-alkylene, $C_4$-$C_{12}$alkylene interrupted by one to three oxygen atoms;
$R_{15}$ is hydrogen, $C_1$-$C_{12}$alkyl or a group

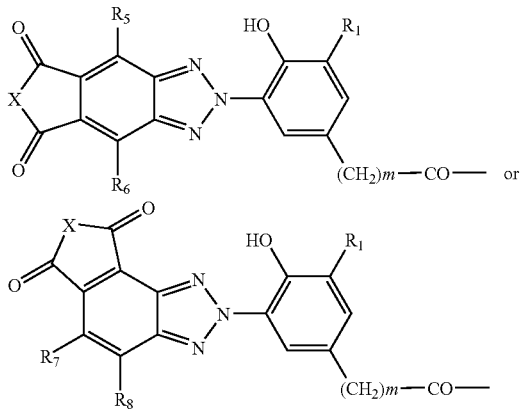

$R_5$, $R_6$, $R_7$ and $R_8$ are independently hydrogen, Cl or Br;

X is O or NE, wherein $E_1$ is hydrogen, straight or branched chain $C_1$-$C_{24}$alkyl, $C_5$-$C_{12}$cycloalkyl, phenyl or $C_7$-$C_{15}$phenylalkyl; or said straight or branched chain $C_1$-$C_{24}$ alkyl or $C_5$-$C_{12}$ cycloalkyl can be substituted by one or more —F, —OH, —$OR_{22}$, —$NH_2$, —$NHR_{22}$, —$N(R_{22})_2$; said phenyl or $C_7$-$C_{15}$phenylalkyl can also be substituted by one or more -halogen, —CN, —$CF_3$, —OH, —$OR_{22}$, —$COR_{22}$, —$R_{22}$; wherein $R_{22}$ is straight or branched chain $C_1$-$C_{18}$ alkyl, straight or branched chain $C_2$-$C_{18}$ alkenyl, $C_5$-$C_{10}$ cycloalkyl, $C_6$-$C_{16}$ phenyl or naphthyl, $C_7$-$C_{15}$ phenylalkyl; or

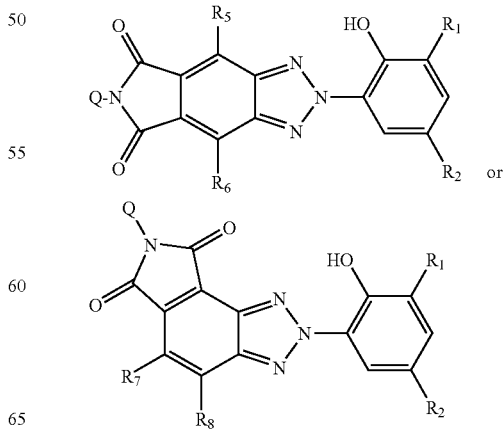

$E_1$ is a group wherein $R_1$ to $R_8$ have the meanings as defined above and

Q is $C_2$-$C_{12}$alkylene, $C_5$-$C_7$cycloalkylene, para-phenylene or a group Particular preference is given to a compound of formula (I) or (II) wherein $R_1$ is hydrogen, straight or branched chain alkyl of 1 to 12 carbon atoms or phenylalkyl of 7 to 15 carbon atoms;

$R_2$ is straight or branched chain alkyl of 1 to 12 carbon atoms or phenylalkyl of 7 to 15 carbon atoms, phenyl, or said phenyl or said phenylalkyl substituted on the phenyl ring by 1 to 3 alkyl of 1 to 4 carbon atoms;

$R_5$ and $R_6$ are hydrogen or one of both is Cl or Br;

$R_7$ and $R_8$ are independently hydrogen, Cl or Br;

X is O or NE, wherein $E_1$ is hydrogen, straight or branched chain $C_1$-$C_6$alkyl, which is unsubstituted or substituted by 1 to 4 OH, phenyl which is unsubstituted or substituted by F, $CF_3$, CN or Cl, or $C_7$-$C_9$phenylalkyl.

A compound of formula (I) is in general preferred.

Individual useful compounds are for example compound 1b and 2c (1b)

(2c)

A further aspect of the invention is a process for the preparation of a compound of formulae (I) or (II)

(I)

(II)

wherein the substituents $R_1$ to $R_8$ are as defined in claim 1, which process comprises reacting a compound of formulae (III), (IV) or (V)

(III)

(IV) or

-continued

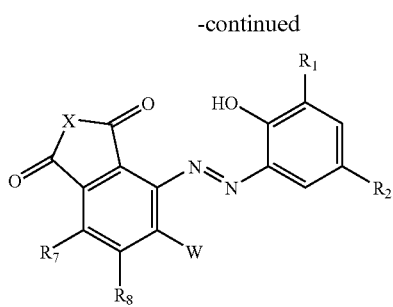
(V)

wherein W is halogen or nitro with an azide compound of formula (X)

$M^{n+}(N_3^-)_r$ (X)

wherein

M is an n-valent metal cation,

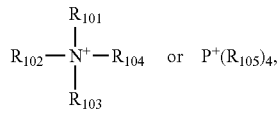

$R_{101}$, $R_{102}$, $R_{103}$ and $R_{104}$ are each independently of the others hydrogen or $C_1$-$C_{18}$alkyl, $R_{105}$ is $C_1$-$C_{18}$alkyl, and r is 1, 2 or 3.

Preferred reaction conditions of the process according to the invention are as follows:

The reaction can be carried out in the melt or in a solvent. Of special interest is a process for the preparation of compounds of formula I or II wherein the reaction is carried out in a solvent.

Suitable solvents are, for example, dipolar aprotic solvents, protic solvents, esters of aliphatic or aromatic carboxylic acids, ethers, halogenated hydrocarbons, aromatic solvents, amines and alkoxybenzenes.

Examples of dipolar aprotic solvents are dialkyl sulfoxides, for example dimethyl sulfoxide; carboxamides, for example formamide, dimethylformamide or N,N-dimethylacetamide; lactams, for example N-methylpyrrolidone; phosphoric amides, for example hexamethylphosphoric triamide; alkylated ureas, for example N,N'-dimethylethyleneurea, N,N'-dimethylpropyleneurea or N,N,N',N'-tetramethylurea; and nitriles, for example acetonitrile or benzonitrile.

Examples of protic solvents are polyalkylene glycols, for example polyethylene glycol; polyalkylene glycol monoethers, for example diethylene glycol monomethyl ether, and water, the latter on its own or in a single-phase or two-phase mixture with one or more of the solvents mentioned, it being possible also for phase transfer catalysts to be added, for example tetraalkylammonium salts, tetraalkylphosphonium salts or crown ethers. The same phase transfer catalysts can also be of use in solid/liquid form in the two-phase system.

Preferred esters of aliphatic or aromatic carboxylic acids are, for example, butyl acetate, cyclohexyl acetate and methyl benzoate.

Preferred ethers are, for example, dialkyl ethers, especially dibutyl ether, tetrahydrofuran, dioxane and (poly-)alkylene glycol dialkyl ethers.

Halogenated hydrocarbons are, for example, methylene chloride and chloroform.

Aromatic solvents are, for example, toluene, chlorobenzene and nitrobenzene.

Suitable amine solvents are, for example, triethylamine, tributylamine and benzyl-dimethylamine.

Preferred alkoxybenzenes are, for example, anisole and phenetole.

The process for the preparation of compounds of formula I can also be carried out in ionic or supercritical fluids, for example fluid carbon dioxide.

Of special interest is a process for the preparation of compounds of formula I or II wherein the reaction is carried out in a dipolar aprotic solvent.

The reaction temperatures can be varied within wide limits but are so selected that satisfactory conversion occurs, such temperatures preferably being from 10° to 200° C., especially from 20° to 150° C.

An analogous process for other benzotriazole compounds has already been disclosed in WO 02/24668.

Preference is given to a process for the preparation of compounds of formula I or II wherein the molar ratio of the amount of compound of formula II, IV or V to the amount of azide compound of formula X is from 1:1 to 1:3, especially from 1:1 to 1:2, e.g. from 1:1 to 1:1.3. When functional side groups that are also able to react with azide are present, the excess of the azide compound of formula IX is increased accordingly.

In a specific embodiment the reaction is carried out in the presence of a catalyst.

Such catalysts include, for example, copper(I) or copper (II) salts or other transition metal salts, based, for example, on iron, cobalt, nickel, palladium, platinum, gold or zinc. Instead of transition metal salts, the anions of which can be varied within wide limits, it is also possible to use metal complexes and metal complex salts of the same metals as catalysts. Preference is given to the use of copper(I) and copper(II) chlorides, bromides and iodides, and special preference to the use of copper(I) bromide.

The catalyst is advantageously used in an amount of from 0.01 to 10% by weight, especially from 0.1 to 5% by weight, e.g. from 0.1 to 5% by weight, based on the weight of the compound of formula II, IV or V employed.

The reaction can also be carried out in the presence of an additional base or in the presence of an alkaline pH buffer system. Suitable pH buffer systems include, for example, alkali metal or alkaline earth metal hydroxides; alkali metal or alkaline earth metal alcoholates; alkali metal or alkaline earth metal carboxylates, for example acetates or carbonates; alkali metal or alkaline earth metal phosphates; tertiary amines, for example triethylamine or tributylamine; and unsubstituted or substituted pyridines.

Some of the starting compounds of formula II, IV or V are known from the literature or can be prepared analogously to the procedures described in Examples 1 and 2.

It is, however, also possible to prepare the instant benzotriazoles by conventional methods for preparing such compounds. The usual procedure involves the diazotization of a substituted o-nitroaniline (W is then $NO_2$) followed by coupling the resultant diazonium salt with a substituted phenol and reduction of the azobenzene intermediate to the corresponding desired benzotriazole. Such processes are described, for example, in U.S. Pat. No. 5,276,161 and U.S. Pat. No. 5,977,219. The starting materials for these benzotriazoles are partly items of commerce or can be prepared by normal methods of organic synthesis.

Further methods for the preparation of benzotriazoles are for example given in Science of Synthesis 13.13, 575-576.

The reduction process can not only be carried out by hydration but also by other methods, such as for example described in EP 0 751 134. When a H-transfer is made, reagents, such as formic acid or its salts, phosphinic acid or its salts or an alkali metal or ammonium salt of hypophosphoric acid together with a catalyst may be useful. The catalyst is, for example, a precious metal.

The benzotriazoles of the present invention are generally useful as UV-absorbers in various substrates. Consequently a further aspect of the invention is a composition stabilized against light-induced degradation which comprises, (a) an organic material subject to light-induced degradation, and (b) a compound of formula I or II as described above.

In general the compound of formula I or II is present in an amount from 0.1% to 30%, preferably from 0.5% to 15% and more preferably from 1% to 10% by weight, based on the weight of the organic material.

In one aspect the organic material is a recording material.

The recording materials according to the invention are suitable for pressure-sensitive copying systems, photocopying systems using microcapsules, heat-sensitive copying systems, photographic materials and ink jet printing.

The recording materials according to the invention are distinguished by an unexpected improvement in quality, especially with regard to the fastness to light.

The recording materials according to the invention have the construction known for the particular use. They consist of a customary carrier, for example paper or plastic film, which has been coated with one or more layers. Depending on the type of the material, these layers contain the appropriate necessary components, in the case of photographic materials, for example, silver halide emulsions, dye couplers, dyes and the like. Material particularly suitable for ink jet printing has a layer particularly absorptive for ink on a customary carrier. Uncoated paper can also be employed for ink jet printing. In this case the paper acts at the same time as the carrier material and as the ink-absorbent layer. Suitable material for ink jet printing is, for example, described in U.S. Pat. No. 5,073,448 (incorporated herein by reference).

The recording material can also be transparent, as, for example, in the case of projection films.

The compounds of the formula I or II can be incorporated into the carder material as early as the production of the latter, in the production of paper, for example, by being added to the paper pulp. A second method of application is to spray the carder material with an aqueous solution of compounds of the formula I or II or to add the compounds of the to the coating composition.

Coating compositions intended for transparent recording materials suitable for projection cannot contain any particles which scatter light, such as pigments and fillers.

The dye-binding coating composition can contain a number of other additives, for example antioxidants, light stabilizers (including also UV absorbers which do not belong to the UV absorbers according to the invention), viscosity improvers, fluorescent brighteners, biocides and/or antistatic agents.

The coating composition is usually prepared as follows: the water-soluble components, for example the binder, are dissolved in water and stirred together. The solid components, for example fillers and other additives already described, are dispersed in this aqueous medium. Dispersion is advantageously carded out by means of devices, for example ultrasonic samples, turbine stirrers, homogenizers, colloid mills, bead mills, sand mills, high-speed stirrers and the like. The compounds of the formula I or II can be incorporated easily into the coating composition.

The recording material according to this invention preferably contains 1 to 5000 mg/m$^2$, in particular 50-1200 mg/m$^2$, of a compound of the formula I.

As already mentioned, the recording materials according to the invention embrace a wide field. The compounds of the formula I or II can, for example, be employed in pressure-sensitive copying systems. They can be introduced either into the paper in order to protect the microencapsulated dye precursors there from light, or into the binder of the developer layer in order to protect the dyes formed there.

Photocopying systems using light-sensitive microcapsules which are developed by means of pressure are described in U.S. Pat. Nos. 4,416,966; 4,483,912; 4,352,200; 4,535,050; 4,536,463; 4,551,407; 4,562,137 and 4,608,330, also in EP-A 139,479; EP-A 162,664; EP-A 164,931; EP-A 237,024; EP-A 237,025 or EP-A 260,129. In all these systems the compounds can be put into the dye-receiving layer. The compounds can, however, also be put into the donor layer in order to protect the colour formers from light.

Photographic materials which can be stabilized are photographic dyes and layers containing such dyes or precursors thereof, for example photographic paper and films. Suitable materials are, for example, described in U.S. Pat. No. 5,364,749 (incorporated therein by reference). The compounds of the formula I or II act here as a UV filter against electrostatic flashes. In colour photographic materials couplers and dyes are also protected against photochemical decomposition.

The instant compounds can be used for all types of colour photographic materials. For example, they can be employed for colour paper, colour reversal paper, direct-positive colour material, colour negative film, colour positive film, colour reversal film, etc. They are preferably used, inter alia, for photographic colour material which contains a reversal substrate or forms positives.

Colour-photographic recording materials usually contain, on a support, a blue-sensitive and/or a green-sensitive and/or a red-sensitive silver-halide emulsion layer and, if desired, a protection layer, the compounds being, preferably, either in the green-sensitive or the red-sensitive layer or in a layer between the green-sensitive and the red-sensitive layer or in a layer on top of the silver-halide emulsion layers.

The compounds of the formula I or II can also be employed in recording materials based on the principles of photopolymerization, photoplasticization or the rupture of microcapsules, or in cases where heat-sensitive and light-sensitive diazonium salts, leuko dyes having an oxidizing agent or dye lactones having Lewis acids are used.

Furthermore, they can be employed in recording materials for dye diffusion transfer printing, thermal wax transfer printing and not matrix printing and for use with electrostatic, electrographic, electrophoretic, magnetographic and laser-electrophotographic printers and pen-plotters. Of the above, recording materials for dye diffusion transfer printing are preferred as, for example described in EP-A-507,734.

They can also be employed in inks, preferably for ink jet printing, as, for example, further described in U.S. Pat. No. 5,098,477 (incorporated herein by reference).

In another specific embodiment of the invention the organic material is a natural, semi-synthetic or synthetic polymer.

Examples of such polymers are given below.

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
  a) radical polymerisation (normally under high pressure and at elevated temperature).
  b) catalytic polymerisation using a catalyst that normally contains one or more than one metal of groups IVb, Vb, VIb or VII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE), and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is gene-rated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfo-chlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polyketones.

21. Polysulfones, polyether sulfones and polyether ketones.

22. Crosslinked polymers derived from aldehydes on the one hand and phenols, ureas and melamines on the other hand, such as phenol/formaldehyde resins, urea/formaldehyde resins and melamine/formaldehyde resins.

23. Drying and non-drying alkyd resins.

24. Unsaturated polyester resins derived from copolyesters of saturated and unsaturated dicarboxylic acids with polyhydric alcohols and vinyl compounds as crosslinking agents, and also halogen-containing modifications thereof of low flammability.

25. Crosslinkable acrylic resins derived from substituted acrylates, for example epoxy acrylates, urethane acrylates or polyester acrylates.

26. Alkyd resins, polyester resins and acrylate resins crosslinked with melamine resins, urea resins, isocyanates, isocyanurates, polyisocyanates or epoxy resins.

27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

For example the polymer is a thermoplastic polymer.

In another embodiment the organic material is a coating, in particular an automotive coating.

Resins used in coatings are typically crosslinked polymers, for example, derived from aldehydes on the one hand and phenols, ureas and melamines on the other hand, such as phenol/formaldehyde resins, urea/formaldehyde resins and melamine/formaldehyde resins.

Also useful are unsaturated polyester resins derived from copolyesters of saturated and unsaturated dicarboxylic acids with polyhydric alcohols and vinyl compounds as crosslinking agents, and also halogen-containing modifications thereof of low flammability.

Preferably used are crosslinkable acrylic resins derived from substituted acrylates, for example epoxy acrylates, urethane acrylates or polyester acrylates.

Also possible are alkyd resins, polyester resins and acrylate resins crosslinked with melamine resins, urea resins, isocyanates, isocyanurates, polyisocyanates or epoxy resins.

Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

The coating material may also be a radiation curable composition containing ethylenically unsaturated monomers or oligomers and a polyunsaturated aliphatic oligomer.

The alkyd resin lacquers which can be stabilized against the action of light in accordance with the instant invention are the conventional stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99-123). Other crosslinking agents include glycouril resins, blocked isocyanates or epoxy resins.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like. Correspondingly, the epoxide may be utilized as the crosslinking agent for various acrylic or polyester resin systems that have been modified by the presence of reactive groups on the backbone structure.

When water-soluble, water miscible or water dispersible coatings are desired ammonium salts of acid groups present in the resin are formed. Powder coating composition can be prepared by reacting glycidyl methacrylate with selected alcohol components.

In a specific embodiment the above mentioned coating is applied over a substrate, which is sensitive to electromagnetic radiation of wavelengths greater than 380 nm.

A typical sensitive substrate is, for example, a cathodically deposited coating adhering to a metal substrate. Such coatings are typically used in the automotive industry.

Under sensitive to electromagnetic radiation of wavelengths greater than 380 nm there is understood UV or visible light, for example, in the wavelength range up to 440 nm, preferably up to 420 nm and in particular up to 410 nm.

In the various organic materials, in which the compounds of formula (I) or (II) are useful as stabilizers against the deleterious influence of UV and/or visible light further stabilizers and additives may be also present.

Examples are subsequently given.

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl) phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis (3,5-di-tert-butyl-4-hydroxyphenyl)adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis [6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3', 5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl) phenyl]-2,2-bis(3,5-di-tert-butyl-4-hydroxybenzyl) malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3, 5,6-tetramethyl benzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4, 6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyidiphenylamine, 4-n-butyl-aminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyidiphenylamines, a mixture of mono- and dialkylated nonyidiphenylamines, a mixture of mono- and dialkylated dodecyldiphenylamines, a mixture of mono- and dialkylated isopropyl/isohexyl-diphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene.

2. UV Absorbers and Light Stabilizers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethyl benzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$, where R=3'-tert-butyl-4'-hydroxy-5'-2H-benzotriazol-2-ylphenyl, 2-[2'-hydroxy-3'-(α,α-dimethyl benzyl)-5'-(1,1,3,3-tetramethylbutyl)-phenyl]-benzotriazole; 2-[2'-hydroxy-3'-(1,1,3,3-tetramethylbutyl)-5'-(α,α-dimethyl benzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butyl phenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxy-cinnamate, N-(β-carbomethoxy-β-cyanovinyl)-2-methylindoline, neopentyl tetra(α-cyano-β,β-diphenylacrylate.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tertoctylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor (Clariant; CAS Reg. No. 106917-31-1], 5-(2-ethylhexanoyl)oxymethyl-3,3,5-trimethyl-2-morpholinone, the reaction product of 2,4-bis-[(1-cyclohexyloxy-2,2,6,6-piperidine-4-yl)butylamino]-6-chloro-s-triazine with N,N'-bis(3-aminopropyl) ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)-amino)-s-triazine.

2.7. Oxamides, for example 4, 4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethyl phenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenyl hydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis (2,4-di-tert-butyl-6-methylphenyl)-pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo-[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:

Tris(2,4-di-tert-butylphenyl) phosphite (Irgafos®168, Ciba Specialty Chemicals Inc.), tris(nonylphenyl) phosphite,

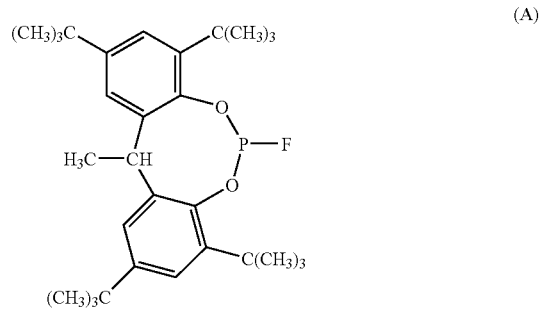

(A)

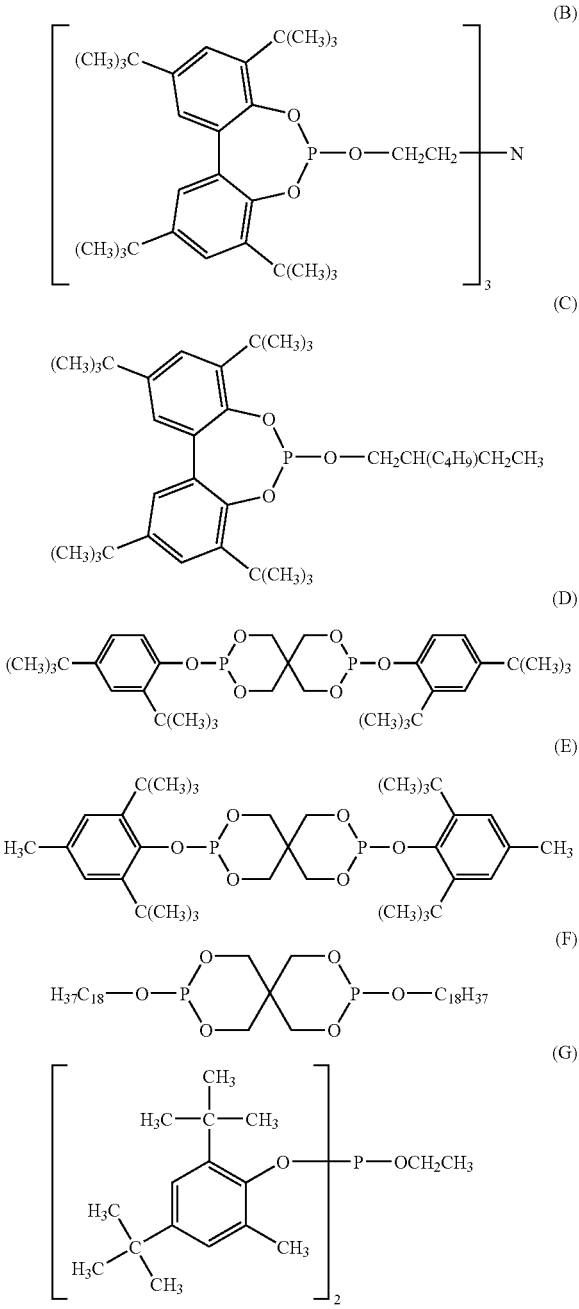

5. Hydroxylamines, for example N,N-dibenzylhydroxylamine, N,N-diethyl hydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenylnitrone, N-ethyl-alpha-methylnitrone, N-octyl-alpha-heptyinitrone, N-lauryl-alpha-undecylnitrone, N-tetradecyl-alpha-tridecylnnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate, dimistryl thiodipropionate, distearyl thiodipropionate or distearyl disulfide.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di(benzylidene)sorbitol.

12. Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839, EP-A-0591102; EP-A-1291384 or 3-[4-(2-acetoxyethoxy)phenyl]-5,7-di-tert-butylbenzofuran-2-one, 5,7-di-tert-butyl-3-[4-(2-stearoyloxyethoxy)phenyl] benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethyl phenyl)-5,7-di-tert-butyl benzofuran-2-one, 3-(3,5-dimethyl-4-pivaloyloxyphenyl)-5,7-di-tert-butylbenzofuran-2-one, 3-(3,4-dimethyl phenyl)-5,7-di-tert-butyl benzofuran-2-one, 3-(2,3-dimethylphenyl)-5,7-di-tert-butylbenzofuran-2-one, 3-(2-acetyl-5-isooctylphenyl)-5-isooctylbenzofuran-2-one.

Preferably the compositions above contain additionally a sterically hindered amine stabilizer and/or a UV absorber selected from the group consisting of the s-triazines, the oxanilides, the hydroxybenzophenones, benzoates, the α-cyanoacrylates and the benzotriazoles different from those of formulae (I) or (II) as described above.

When additional UV-absorbers are added they are preferably added in an amount from 0.1% to 30%, more preferably from 0.5% to 15% and most preferably from 1% to 10% by weight, based on the weight of the organic material.

When a hindered amine light stabilizer is additionally added it is preferably added in an amount from 0.1% to 10%, more preferably from 0.5% to 5% and most preferably from 1% to 3% by weight, based on the weight of the organic material.

The total amount of UV-absorber of formula I or II and other UV-absorbers and/or hindered amine stabilizer is for example from 0.5% to 15% by weight, based on the weight of the organic material.

Examples for the hindered amine light stabilizers and UV-absorbers of the different classes are given above.

Particularly preferred UV-absorbers are the following s-triazines and benzotriazoles:

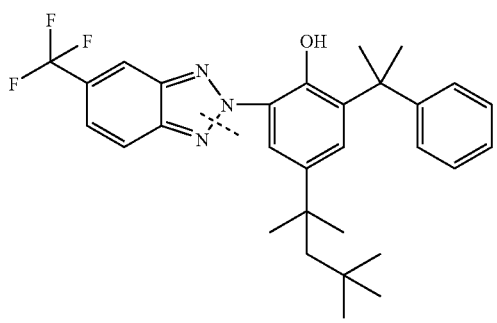

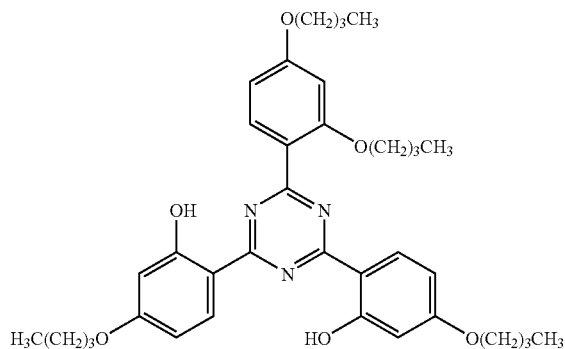

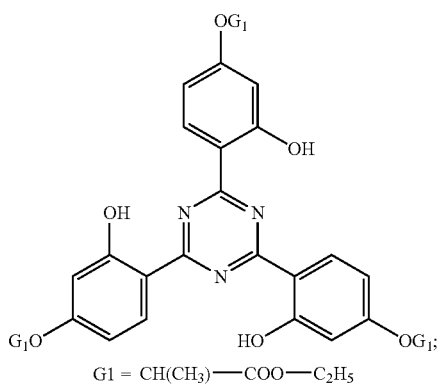

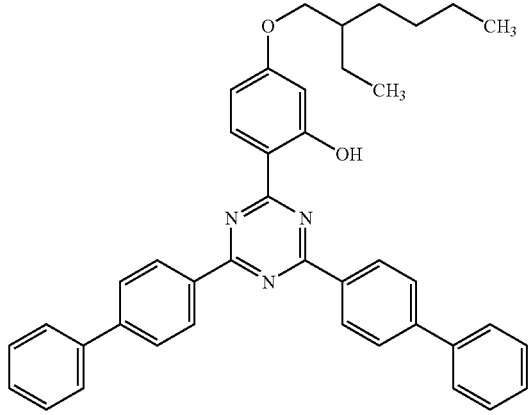

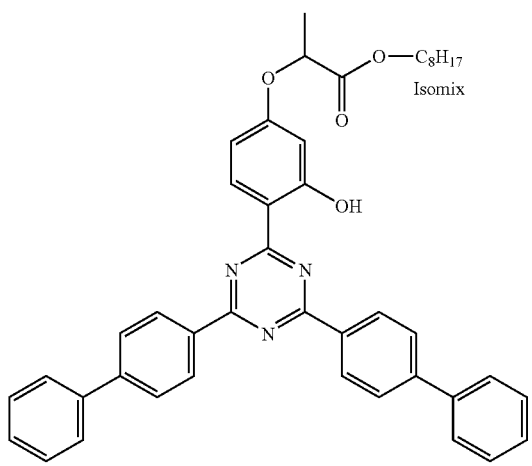

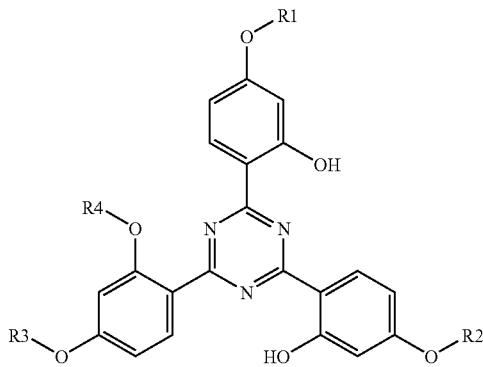
= a mixture of
a) R1 = R2 = CH(CH$_3$)—COO—C$_8$H$_{17}$, R3 = R4 = H;
b) R1 = R2 = R3 = CH(CH$_3$)—COO—C$_8$H$_{17}$, R4 = H;
c) R1 = R2 = R3 = R4 = CH(CH$_3$)—COO—C$_8$H$_{17}$
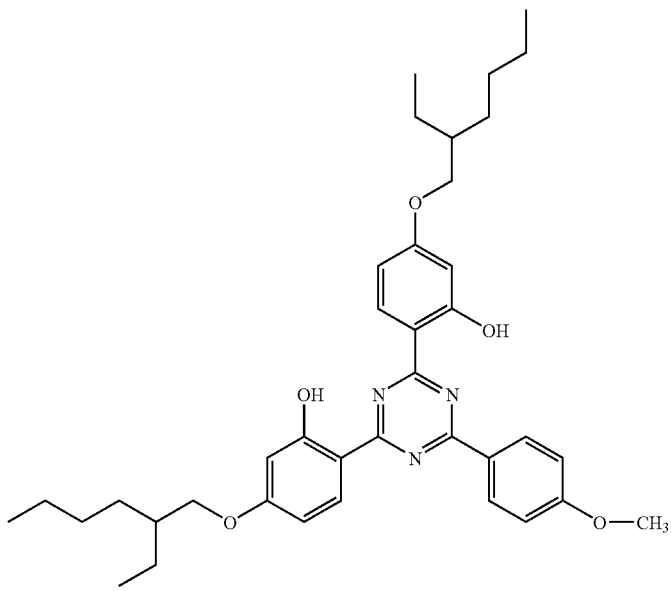
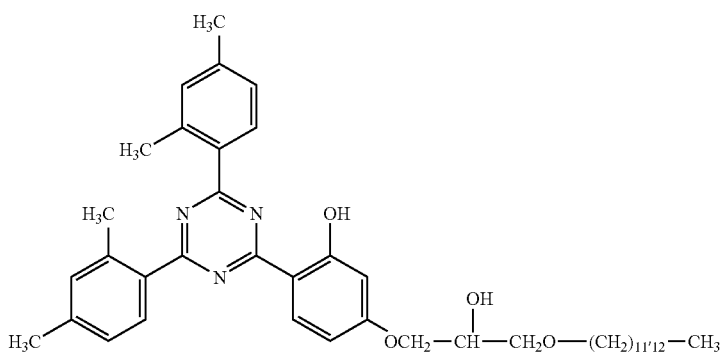

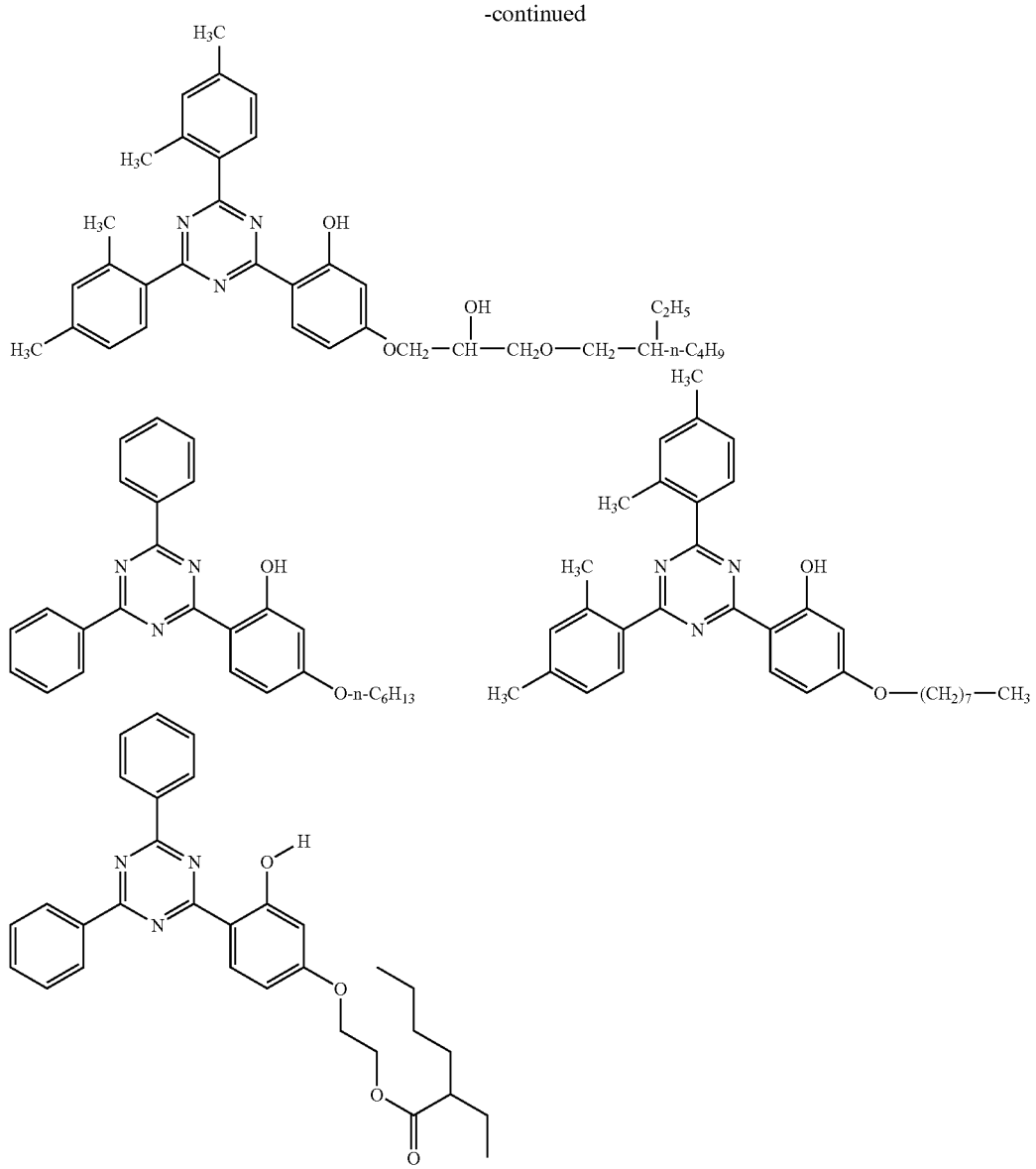

The hydroxyphenyl triazine UV-absorbers are known and are partially items of commerce.

The most suitable benzotriazole UV-absorbers are commercially available under the Trade Names TINUVIN 384®, TINUVIN 928®, TINUVIN 900®, TINUVIN 328® and TINUVIN 1130®.

The sterically hindered amine compounds of component (c) are preferably selected from the group consisting of the following commercial products:

DASTIB 845®, TINUVIN 770®, TINUVIN 765®, TINUVIN 144®, TINUVIN 123®, TINUVIN 111®, TINUVIN 783®, TINUVIN 791®, TINUVIN 123®, TINUVIN 292®, TINUVIN 152®, TINUVIN 144®, MARK LA 52®, MARK LA 57®, MARK LA 62®, MARK LA 67®, HOSTAVIN N 20®, HOSTAVIN N 24®, SANDUVOR 3050®, SANDUVOR 3058®, DIACETAM 5®, SUMISORB™ 61®, UVINUL 4049®, SANDUVOR PR 31®, GOODRITE UV 3034®, GOODRITE UV 3150®, GOODRITE UV 3159®, GOODRITE 3110×128α, UVINUL 4050 Hα, CHIMASSORB 944α, CHIMASSORB 2020α, CYASORB UV 3346®, CYASORB UV 3529®, DASTIB 1082®, CHIMASSORB 119®, UVASIL 299®, UVASIL 125®, UVASIL 2000®, UVINUL 5050 H®, LICHTSCHUTZSTOFF UV 31®, LUCHEM HA B 18®, MARK LA 63®, MARK LA 68®, UVASORB HA 88®, TINUVIN 622®, HOSTAVIN N 30® and FERRO AM 806®.

Particularly preferred are TINUVIN 770®, TINUVIN 292®, TINUVIN 123®, TINUVIN 144® and TINUVIN 152®.

Yet another aspect of the invention is the use of a compound of formula I or II as ultraviolet (UV) and visible (VIS) light absorber in organic materials.

The definitions and preferences given for the compounds apply also for the other aspects of the invention.

The following examples illustrate the invention.

A) PREPARATION EXAMPLES

Example A1

Preparation of Hydroxyphenylbenzotriazol 1b

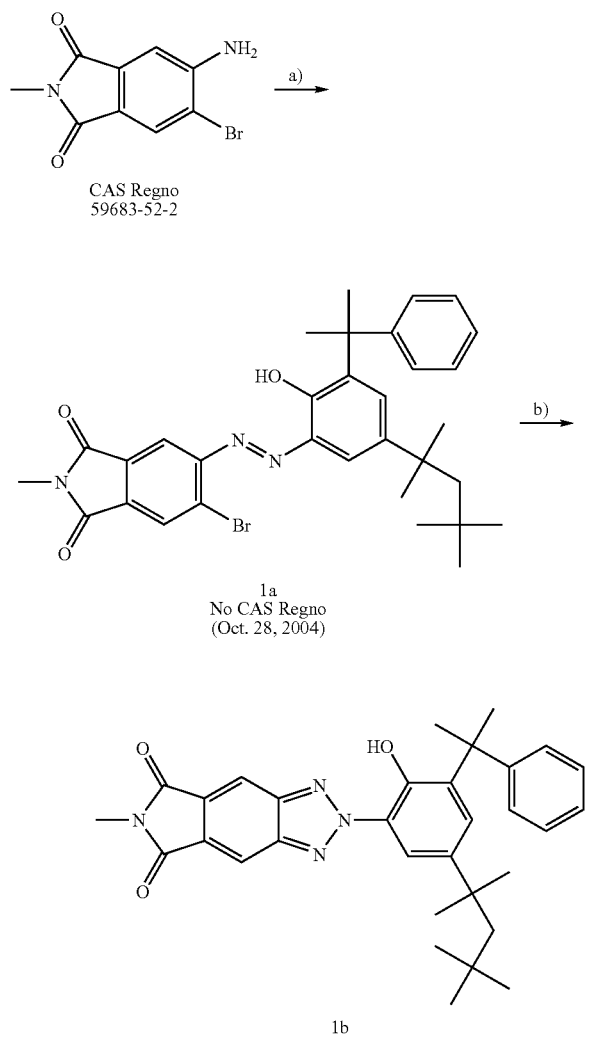

a) Nitrosylsulfuric acid (40% in sulfuric acid; 14.0 g, 44.1 mmol) is slowly added at 15° C. to a stirred suspension of 4-amino-5-bromophtalimide (95%; 10.7 g, 39.9 mmol) in acetic acid (200 ml). During the addition the temperature of the reaction mixture is kept between 15° C. and 17° C. by means of an ice bath. After the addition is complete (three quarters of an hour), stirring is continued for two hours. The reaction mixture is then transferred into a dropping funnel and slowly added at −15° C. to a stirred solution of 2-cumyl-4-t-octylphenol (95%; 13.7 g, 40.1 mmol) in methanol/m-xylene (85/15 by volume; 200 ml) containing sodium hydroxide microprills (1.8 g, 45.0 mmol) and sodium acetate (13.1 g, 159.7 mmol). During the addition, the temperature of the reaction mixture is kept between −15° C. and −9° C. by means of an isopropanol-dry ice bath; the pH is measured by means of an electrode and held above 5 by concomitant addition of sodium hydroxide (30% in water; total of 250 ml). After the addition is complete (two hours; initial pH 13.7, final pH 5.6), the cooling bath is removed and the red suspension stirred overnight. Water (150 ml) and toluene (250 ml) are added, the water phase split off and washed with toluene (1×250 ml). The combined organic phases are washed with water (2×250 ml), dried (MgSO$_4$), filtered and the solvent evaporated affording 30 g of a red oil. Methanol (60 g) is added and the suspension heated to reflux. Upon cooling (ice bath), compound 1a crystallizes as red solid, which is filtered off, washed with methanol and dried.

Yield 16.2 g (27.4 mmol, 68.8%).

Melting point: 178-179° C.

$^1$H-NMR (300 MHz, CD$_2$Cl$_2$), δ (ppm): 13.14 (s, 1H), 8.34 (s, 1H), 8.18 (s, 1H), 7.92 (d-like, 1H), 7.76 (d-like, 1H), 7.28-7.24 (m, 4H), 7.20-7.15 (m, 1H), 3.20 (s, 3H), 1.87 (s, 2H), 1.82 (s, 6H), 1.51 (s, 6H), 0.86 (s, 9H).

b) A stirred mixture of compound 1a (17.2 g, 29.1 mmol), sodium azide (99%; 2.5 g, 38.1 mmol) and 1-methyl-2-pyrrolidinone (60 ml) is heated to 120° C. The temperature is maintained until evolution of nitrogen ceases (1.5 hours). The dark solution is cooled to 25° C. followed by the addition of water (100 ml) and toluene (150 ml). The water phase is split off and washed with toluene (1×50 ml). The combined organic phases are washed with water (3×50 ml), dried (MgSO$_4$), filtered and the solvent evaporated affording 17 g of a viscous red oil which solidifies upon standing. The crude material is dissolved in hot toluene. Hexane is added and the solution cooled whereas compound 1b crystallizes as yellowish solid, which is filtered off and dried (8 g). The filtrate is evaporated to dryness and the residue crystallized from hexane to afford another 3.5 g. Yield 11.5 g (21.9 mmol, 75.3%).

Melting point: 198-199° C.

$^1$H-NMR (300 MHz, CD$_2$Cl$_2$), δ (ppm): 10.97 (s, 1H), 8.40-8.39 (m, 3H), 7.76 (d-like, 1H), 7.31-7.24 (m, 4H), 7.20-7.15 (m, 1H), 3.25 (s, 3H), 1.91 (s, 2H), 1.83 (s, 6H), 1.54 (s, 6H), 0.86 (s, 9H).

Example A2

Preparation of Hydroxyphenylbenzotriazol 2c

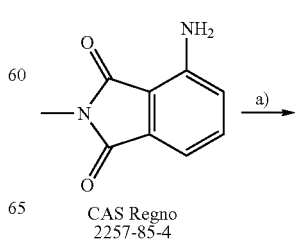

-continued

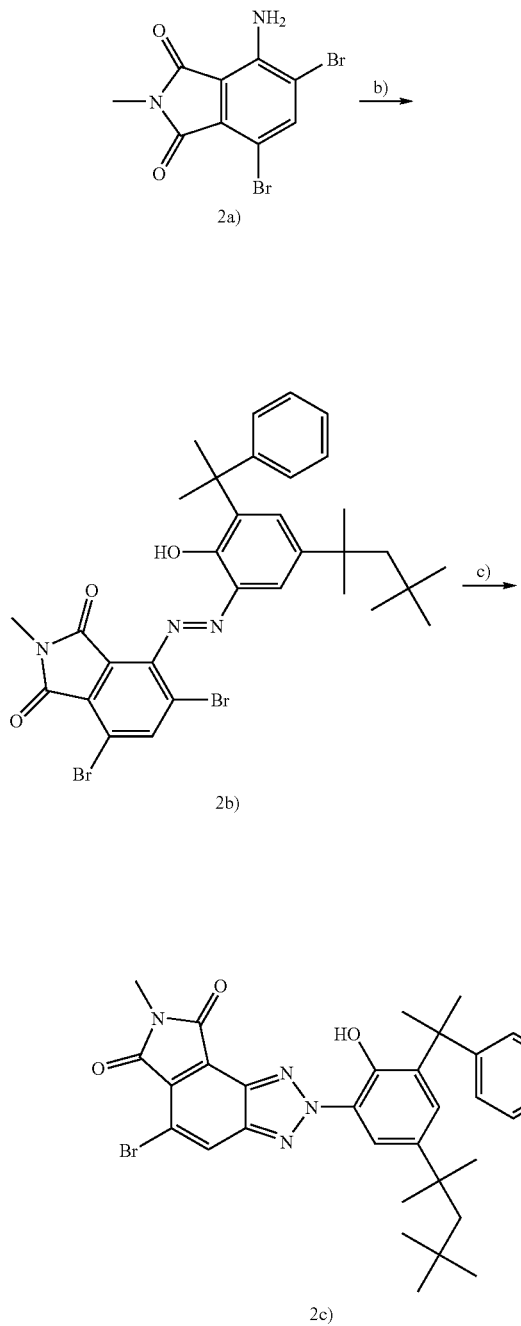

a) A mixture of 4-amino-N-methylphthalimid (17.8 g, 10.0 mmol), sodium acetate (1.64 g, 20 mmol) and acetic acid (30 g) are stirred together at room temperature. Bromine (3.22 g, 20 mmol) in acetic acid (10 ml) is added dropwise with good stirring. A precipitate forms after about one-half of the bromine has been added. Stirring is continued for 16 h after the complete addition of the bromine. Then water is added (40 ml) and the product is collected by filtration, washed with water (10 ml) and dried.

Yield: 3.18 g (95%).

Melting point: 216° C.-218° C.

$^1$H-NMR (300 MHz, DMSO-d$_6$), δ (ppm): 7.92 (s, 1H), 6.46 (s, broad, 2H), 2.96 (s, 3H).

b) Nitrosylsulfuric acid (40% in sulfuric acid; 14.0 g, 44.1 mmol) is slowly added at 15° C. to a stirred suspension of 3-amino-4,6-dibromophtalimide (13.4 g, 40.0 mmol) in acetic acid (200 ml). During the addition the temperature of the reaction mixture is kept between 15° C. and 17° C. by means of an ice bath. After the addition is complete (three quarters of an hour), stirring is continued for one hour. The reaction mixture is then transferred into a dropping funnel and slowly added at −15° C. to a stirred solution of 2-cumyl-4-t-octylphenol (95%; 13.7 g, 40.1 mmol) in methanol/m-xylene (85/15 by volume; 200 ml) containing sodium hydroxide microprills (1.8 g, 45.0 mmol) and sodium acetate (13.1 g, 159.7 mmol). During the addition, the temperature of the reaction mixture is kept between −15° C. and −9° C. by means of an isopropanol-dry ice bath; the pH is measured by means of an electrode and held above 5 by concomitant addition of sodium hydroxide (30% in water; total of 250 ml). After the addition is complete (two hours; initial pH 13.7, final pH 5.6), the cooling bath is removed and the red suspension stirred overnight. Compound 2b, which crystallizes as red solid, is filtered off, washed with isopropanolol and dried.

Yield 16.6 g (62.0%).

Melting point: 180° C. (dec.)

$^1$H-NMR (300 MHz, CDCl$_3$), δ (ppm): 11.70 (s, 1H), 8.14 (s, 1H), 7.78 (d-like, 1H), 7.70 (d-like, 1H), 7.30-7.28 (m, 4H), 7.21-7.17 (m, 1H), 3.16 (s, 3H), 1.82 (s, 6H), 1.81 (s, 2H), 1.46 (s, 6H), 0.83 (s, 9H).

c) A stirred mixture of compound 2b (6.70 g, 10 mmol), sodium azide (99%; 0.85 g, 13 mmol) and 1-methyl-2-pyrrolidinone (25 ml) is heated to 50° C. The temperature is maintained until evolution of nitrogen ceases (2 hours). The dark solution is cooled to 25° C. followed by the addition of water (25 ml) and ethyl acetate (50 ml). The water phase is split off and the product, which precipitates in the ethyl acetate, is collected by filtration. The crude material is recrystallized from hot toluene (20 ml), filtered off and dried.

Yield 1.05 g (17.4%).

Melting point: 221° C.-225° C. (dec.).

$^1$H-NMR (300 MHz, CDCl$_3$), δ (ppm): 10.89 (s, 1H), 8.41 (s, 1H) 8.39 (d-like, 1H), 7.74 (d-like, 1H), 7.29-7.26 (m, 4H), 7.22-7.17 (m, 1H), 3.26 (s, 3H), 1.87 (s, 2H), 1.84 (s, 6H), 1.53 (s, 6H), 0.84 (s, 9H).

Example A3

Preparation of Hydroxyphenlybenzotriazols 3d(I)-3d(V) from imide 1b via dicarboxylic acid 3a and anhydride 3b, without isolation of intermediate amic acids 3c(I)-3c(V)

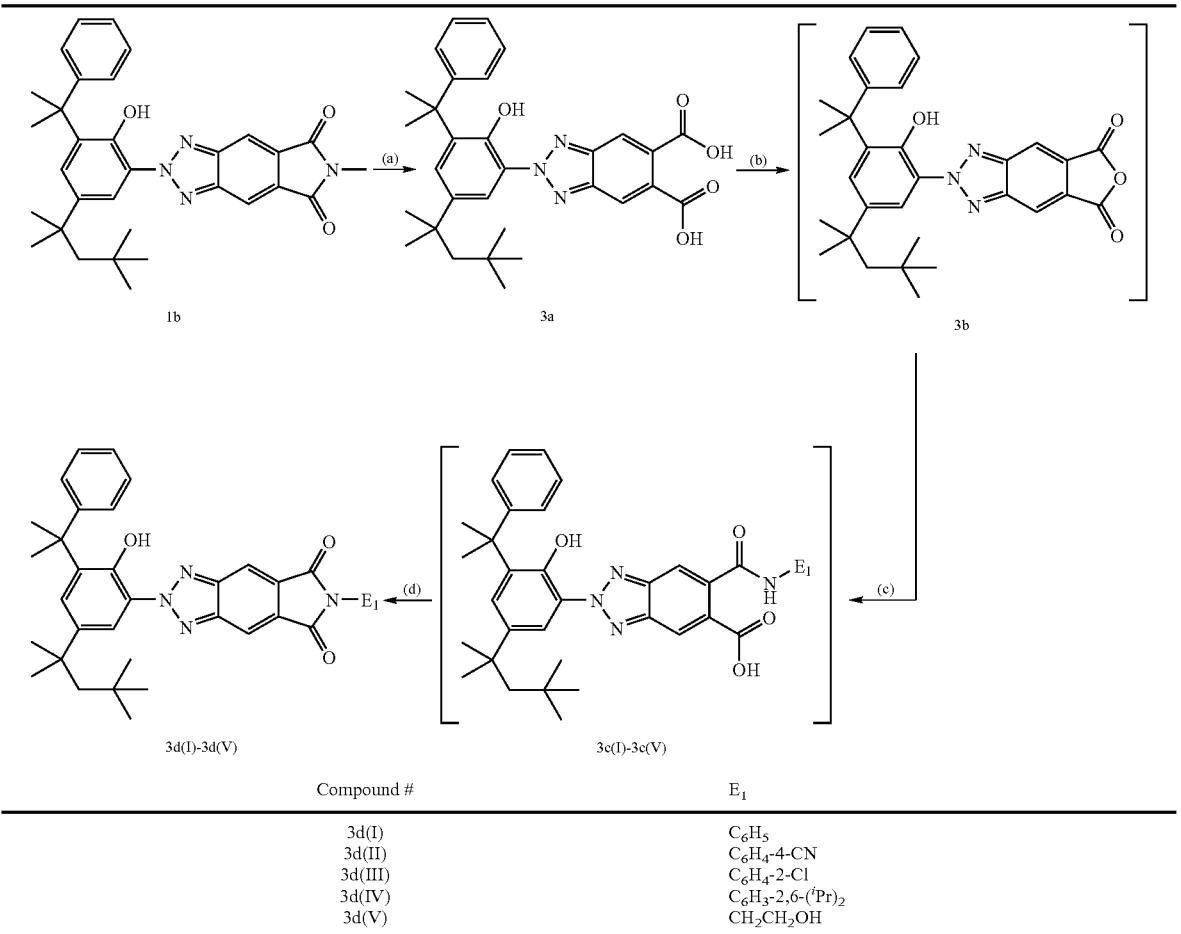

| Compound # | $E_1$ |
|---|---|
| 3d(I) | $C_6H_5$ |
| 3d(II) | $C_6H_4$-4-CN |
| 3d(III) | $C_6H_4$-2-Cl |
| 3d(IV) | $C_6H_3$-2,6-($^i$Pr)$_2$ |
| 3d(V) | $CH_2CH_2OH$ |

The intermediate compound of formula 3a and their analogous compounds are also useful as UV-absorbers.

a) KOH (53.3 g, 950 mmol) is added slowly at 25° C. to a stirred mixture of 1b (49.8 g, 94.9 mmol) and ethanol/water (1/1 by volume; total of 200 g plus 40 ml). After further dilution with ethanol (50 ml) the mixture is brought to 80° C., where it is held for 19.75 hours. Further KOH (2.65 g, 47.2 mmol) is added and stirring at 80° C. continued for another 29 hours. Ethanol is then distilled off on a rotary evaporator and the resulting orange suspension diluted with water (500 ml). The mixture is acidified (pH 2) by slow addition of HCl (aqueous 32% w/w) and the yellow precipitate filtered off. The filter-cake is washed with water (3×100 ml) and dried in a vacuum oven at 40° C. to afford 3a as a yellow solid (53.3 g).

Melting point: 150-175° C. (dec.) HPLC-UV/APCI-MS negative: 529.3 (M); calcd. for $C_{31}H_{35}N_3O_5$: 529.3

$^1$H-NMR (300 MHz, DMSO-d$_6$), δ (ppm): 10.38 (s, 1H), 8.57 (br s, 2H), 7.98 (d, J=1.9 Hz, 1H), 7.64 (d, J=1.9 Hz, 1H), 7.26-7.18 (m, 4H), 7.14-7.08 (m, 1H), 1.80 (s, 2H), 1.75 (s, 6H), 1.43 (s, 6H), 0.78 (s, 9H).

b)-d); 3d(I): A stirred mixture of 3a (4.2 g, 7.9 mmol) and toluene (40 g) is brought to and held at reflux until formation of water, which is separated off by means of a Dean-Stark trap, has ceased (3.75 hours; $t_1$). Aniline (98%; 0.83 g, 8.7 mmol) is then added and the mixture refluxed for another 1.25 hours ($t_2$). Toluene is distilled off on a rotary evaporator and the residue purified by chromatography (silica gel, hexane/toluene/ethylacetate 9/0.5/1) to afford 3d(I) as yellow solid (2.4 g, 51.6%).

Melting point: 220-221° C.

Anal. calcd. for $C_{37}H_{38}N_4O_3$ (586.74): C, 75.74; H, 6.53; N, 9.55. Found: C, 75.52; H, 6.53; N, 9.28.

$^1$H-NMR (400 MHz, DMSO-d$_6$), δ (ppm): 10.26 (br s, 1H), 8.68 (s, 2H), 7.96 (d, J=1.8 Hz, 1H), 7.69 (d, J=1.8 Hz, 1H), 7.56-7.45 (m, 5H), 7.26-7.20 (m, 4H), 7.14-7.10 (m, 1H), 1.82 (s, 2H), 1.76 (s, 6H), 1.45 (s, 6H), 0.79 (s, 9H).

b)-d); 3d(II): Prepared similarly to 3d(I) from 3a (6.35 g, 12.0 mmol), toluene (70 g) and 4-aminobenzonitrile (97%; 1.6 g, 13.1 mmol), reflux lasting 1.1 hours ($t_1$) and 2.25 hours ($t_2$), respectively. Purification of the residue by chromatography (silica gel, toluene) affords 3d(II) as yellow solid (4.2 g, 57.3%).

Melting point: 252-253° C.

Anal. calcd. for $C_{38}H_{37}N_5O_3$ (611.75): C, 74.61; H, 6.10; N, 11.45. Found: C, 74.04; H, 5.83; N, 11.37.

$^1$H-NMR (400 MHz, DMSO-$d_6$), δ (ppm): 10.24 (br s, 1H), 8.72 (s, 2H), 8.05 (d, J=8.5 Hz, 2H), 7.95 (d, J=1.8 Hz, 1H), 7.76 (d, J=8.5 Hz, 2H), 7.69 (d, J=1.8 Hz, 1H), 7.26-7.18 (m, 4H), 7.16-7.10 (m, 1H), 1.82 (s, 2H), 1.76 (s, 6H), 1.44 (s, 6H), 0.79 (s, 9H).

b)-d); 3d(III): Prepared similarly to 3d(I) from 3a (6.35 g, 12.0 mmol), toluene (70 g) and 2-chloroaniline (98%; 1.7 g, 13.1 mmol), reflux lasting 1.0 hour ($t_1$) and 3.25 hours ($t_2$), respectively. Purification of the residue by chromatography (silica gel, toluene/ethylacetate 9/1) affords 3d(III) as yellow solid (2.2 g, 29.5%).

Melting point: 179-180° C.

Anal. calcd. for $C_{37}H_{37}ClN_4O_3$ (621.19): C, 71.54; H, 6.00; Cl, 5.71; N, 9.02. Found: C, 71.04; H, 5.90; Cl, 5.93; N, 8.89.

$^1$H-NMR (300 MHz, DMSO-$d_6$), δ (ppm): 10.22 (s, 1H), 8.76 (s, 2H), 7.95 (d, J=2.1 Hz, 1H), 7.75-7.67 (m, 3H), 7.62-7.53 (m, 2H), 7.27-7.19 (m, 4H), 7.15-7.09 (m, 1H), 1.82 (s, 2H), 1.76 (s, 6H), 1.45 (s, 6H), 0.79 (s, 9H).

b)-d); 3d(IV): Prepared similarly to 3d(1) from 3a (6.35 g, 12.0 mmol), toluene (70 g) and 2,6-diisopropylaniline (90%; 2.6 g, 13.2 mmol), reflux lasting 1.0 hour ($t_1$) and 3.0 hours ($t_2$), respectively. Purification of the residue by chromatography (silica gel, toluene) affords 3d(IV) as yellow solid (3.3 g, 41.0%).

Melting point: 210-211° C.

Anal. calcd. for $C_{43}H_{50}N_4O_3$ (670.90): C, 76.98; H, 7.51; N, 8.35. Found: C, 76.70; H, 7.47; N, 8.29.

$^1$H-NMR (300 MHz, $CD_2Cl_2$), δ (ppm): 11.03 (s, 1H), 8.53 (s, 2H), 8.45 (d, J=2.4 Hz, 1H), 7.79 (d, J=2.4 Hz, 1H), 7.58-7.53 (m, 1H), 7.39-7.36 (m, 2H), 7.33-7.26 (m, 4H), 7.22-7.16 (m, 1H), 2.78 (septet, J=6.8 Hz, 2H), 1.93 (s, 2H), 1.85 (s, 6H), 1.56 (s, 6H), 1.19 (d, J=6.8 Hz, 12H), 0.88 (s, 9H).

b)-d); 3d(V): Prepared similarly to 3d(1) from 3a (6.35 g, 12.0 mmol), toluene (70 g) and ethanolamine (99%; 0.81 g, 13.1 mmol), reflux lasting 1.25 hours ($t_1$) and 1.5 hours ($t_2$), respectively. Purification of the residue by chromatography (silica gel, toluene) affords 3d(V) as yellow solid (2.8 g, 42.1%).

Melting point: 161-162° C.

Anal. calcd. for $C_{33}H_{38}N_4O_4$ (554.70): C, 71.46; H, 6.90; N, 10.10. Found: C, 71.07; H, 6.92; N, 10.03.

$^1$H-NMR (300 MHz, DMSO-$d_6$), δ (ppm): 10.23 (s, 1H), 8.57 (s, 2H), 7.94 (d, J=2.2 Hz, 1H), 7.67 (d, J=2.2 Hz, 1H), 7.26-7.18 (m, 4H), 7.14-7.08 (m, 1H), 4.88 (t, J=5.9 Hz, 1H), 3.72-3.59 (m, 4H), 1.81 (s, 2H), 1.75 (s, 6H), 1.44 (s, 6H), 0.78 (s, 9H).

b) A mixture of N,N'-dicyclohexylcarbodiimide (99%; 2.7 g, 13.0 mmol), 3a (6.35 g, 12.0 mmol) and dichloromethane (40 ml) is stirred at 25° C. for one hour. N,N'-dicyclohexylurea is filtered off and the dichloromethane distilled off on a rotary evaporator to afford 3b as yellow solid (5.5 g, 89.6%).

Melting point: 145-160° C. (dec.)

HPLC-UV/APCI-MS negative: 511.2 (M); calcd. for $C_{31}H_{33}N_3O_4$: 511.2

$^1$H-NMR (300 MHz, $CD_2Cl_2$), δ (ppm): 10.89 (s, 1H), 8.63 (s, 2H), 8.44 (d, J=2.3 Hz, 1H), 7.81 (d, J=2.3 Hz, 1H), 7.31-7.24 (m, 4H), 7.22-7.15 (m, 1H), 1.91 (s, 2H), 1.84 (s, 6H), 1.55 (s, 6H), 0.86 (s, 9H).

B) APPLICATION EXAMPLES

Materials Used

| Acryl/Melamine Clearcoat formulation: | |
|---|---|
| a) Viacryl ® SC 303[1] (65% solution in xylene/butanol, 26:9 wt./wt.) | 27.51 g |
| b) Viacryl ® SC 370[2] (75% in Solvesso 100[3]) | 23.34 g |
| c) Maprenal ® MF 650[4] (55% in isobutanol) | 27.29 g |
| d) Butylacaetate/butanol (37:8 wt./wt.) | 4.33 g |
| e) Isobutanol | 4.87 g |
| f) Solvesso ® 150[5] | 2.72 g |
| g) Crystal oil 30[6] | 8.74 g |
| h) Baysilone ® MA[7] (1% in Solvesso ® 150) | 1.20 g |
| Total | 100.00 g |

Binder raw materials:
[1]Viacryl ® SC 303: acrylic resin (Solutia, formerly Vianova Resins)
[2]Viacryl ® SC 370: acrylic resin (Solutia, formerly Vianova Resins)
[3]Solvesso ® 100: aromatic hydrocarbon, bp. 163-180° C. (Exxon Corp.)
[4]Maprenal ® MF 650: melamine resin (Solutia, formerly Vianova Resins)
[5]Solvesso ® 150: aromatic hydrocarbon, bp. 180-203° C. (Exxon Corp.)
[6]Crystal oil 30: aliphatic hydrocarbon, bp. 145-200° C. (Shell Corp.)
[7]Baysilone ® MA: leveling agent (Bayer AG)

UV-Absorbers and Other Stabilizers

Tinuvin 384®, commercial UV-Absorber from Ciba Specialty Chemicals.

Tinuvin 928®, commercial UV-absorber from Ciba Specialty Chemicals.

Tinuvin 400®, commercial UV-Absorber from Ciba Specialty Chemicals.

Tinuvin 109®, commercial UV-absorber from Ciba Specialty Chemicals.

Oxanilide is Sanduvor 3206

Compounds 1b and 3d (I)-(V) of example A1 and A3 are UV-absorbers according to the invention.

Tinuvin 152®, hindered amine stabilizer from Ciba Specialty Chemicals.

Example B1

Photo Permanence of UV-Absorbers

The photo permanence of the UV-absorbers is evaluated as follows:

the UV-absorbers of the present invention are incorporated into a thermosetting acryl/melamine clear coat (based on Viacryl® SC 303/Viacryl® SC 370/Maprenal® MF 650) in a concentration of 3% based on the solids content of the formulation (solids content: 50.4%). The clear coat is sprayed onto glass plates resulting in a dry film thickness of the clear coat of 20 μm after cure (130° C./30').

Prior to exposure of the specimens, the UV-absorption spectra are recorded using a UV/VIS spectrometer (Perkin Elmer, Lamda 40). Reference: unstabilized acryl/melamine clear coat. Subsequently the specimens are exposed in a Xenon-WOM weatherometer (Atlas Corp.) according to SAE J 1960. The percentage of UV-absorber retained (determined at λ max.) upon exposure is monitored by recording the UV-absorption spectra after regular exposure intervals. The test results are summarized in Table 1.

TABLE 1

Photo permanence of UV-absorbers during Xe—WOM exposure

| Sample | % UV-absorber retained after . . . hours Xe—WOM exposure | | | | |
|---|---|---|---|---|---|
| | 1000 | 1500 | 2000 | 3000 | 4000 h |
| Compound 1B of Example A1 | 92.7 | 86.4 | 82.5 | 76.9 | 72.9 |
| Tinuvin ® 384 | 68.3 | 50.8 | 40.2 | 18.7 | |
| Tinuvin ® 928 | 83.0 | n.a. | 68.2 | 43.4 | |
| Tinuvin ® 400 | 89.8 | 82.1 | 76.0 | 59.4 | |
| Oxanilide | 8 | | | | |

Example B2

Photo Permanence with Protective Overcoat

In a second example two subsequent clear coats are applied on top of each other. The first clear coat (Clear coat I) is stabilized and applied as described in greater detail in example B1. A second thermosetting acryl/melamine clear coat (based on Viacryl® SC 303/Viacryl® SC 370/Maprenal® MF 650) is subsequently sprayed onto the first clear coat resulting in a dry film thickness of the second clear coat (clear coat II) of 40 μm after cure (130° C./30'). The second clear coat is stabilized using a UV-absorber combination of 3% Tinuvin 109/1.5% Tinuvin 400 and 1% Tinuvin 152 as co-stabilizer (HALS). Reference: unstabilized first clear coat. As described in example B1, the UV-transmission spectra are recorded prior to exposure of the specimens using a UV/VIS spectrometer (Perkin Elmer, Lamda 40). Subsequently the specimens are exposed in a Xenon-WOM weatherometer (Atlas Corp.) according to SAE J 1960. The transmission values (determined at 396 nm) as a function of the exposure period are monitored by recording the transmission spectra after regular exposure intervals. The test results are summarized in Table 2:

TABLE 2

Transmission values (determined at 396 nm) as a function of exposure intervals during Xe—WOM exposure

| Sample | transmission values (%) after . . . hours | | | | |
|---|---|---|---|---|---|
| | initial | 1000 | 2000 | 3000 | 4000 |
| Clear coat I: | | | | | |
| unstabilized | | | | | |
| Clear coat II: | | | | | |
| 3% Tinuvin 109/ 1.5% Tinuvin 400 | 21.3 | 24.3 | 25.4 | 26.4 | 28.1 |
| Clear coat I: | | | | | |
| 3% compound 1B | | | | | |
| Clear coat II: | | | | | |
| 3% Tinuvin 109/ 1.5% Tinuvin 400 | 0.44 | 0.49 | 0.55 | 0.59 | 0.63 |

Example B3

Clear Coat Application Over Cathodic Electro Coat

A thermosetting acryl/melamine clear coat is prepared as described in example B1. The paint is sprayed onto electro coated aluminium panels (ED 6950A, 10×30 cm) as commercially available from ACT Laboratories (ACT Laboratories, Inc., South-field, Mich. 48 075, USA) resulting after cure (130° C./30') in a dry film thickness of 20 μm. The panels are subsequently exposed in a Xenon-WOM weatherometer (Atlas Corp.) according to SAE J 1960. The degree of UV-protection of the electro coat underneath the clear coat is monitored at regular exposure intervals as a function of the yellowing (b* value according to DIN 6174) of the electro coat. The results are summarized in Table 3:

TABLE 3

Yellowing of electro coats as a function of clear coat stabilization

| Sample | Δb* versus unexposed after . . . hours Xe—WOM exposure | | | | | |
|---|---|---|---|---|---|---|
| | 200 | 400 | 600 | 800 | 1000 | 1500 |
| without | +4.83 | +5.78 | clear coat delamination | | | |
| 3% Tinuvin 109/ 1.5% Tinuvin 400 | −0.5 | −0.38 | −0.1 | +0.46 | +1.03 | +2.37 |
| 3% compound 1B | −0.68 | −0.69 | −0.60 | −0.45 | −0.31 | −0.22 |

The results clearly show:

a) a significant yellowing/UV-light induced degradation of the electro coat without suitable UV-protection b) insufficient protection of the electro coat with existing UV-absorber packages (Tinuvin 109/Tinuvin 400), which cut out all UV-light in between 300-385 nm c) excellent protection of the electro coat with UV-absorbers with pronounced absorption into the visible wavelength region.

Example B4

Adhesion of Clear Coats Applied Onto Electrocoats

As described in greater detail in example 2, two subsequent clear coat layers are applied on top of electrocoated aluminum panels (ED 6950A, 10×30 cm) as commercially available from ACT Laboratories (ACT Laboratories, Inc., South-field, Mich. 48 075, USA). References: a) both clear coat layers unstabilized, b) second clear coat stabilized with existing UV-absorber package based on Tinuvin 109/Tinuvin 400, i.e. cutting out all UV-light in between 300-385 nm.

Subsequently the specimens are exposed in a Xenon-WOM wetherometer (Atlas Corp.) according to SAE J 1960. The adhesion between the clear coats and the light sensitive electro coat is determined at regular intervals by cross hatch (ISO 2409) followed by tape test. The test results are summarized in Table 4

TABLE 4

Adhesion of clear coats on electrocoats after weathering

| Sample | Cross hatch value (ISO 2409 after . . . hours | | | |
|---|---|---|---|---|
| | 250 h | 1000 h | 1500 h | 2000 h |
| Clear coat I/II unstabilized | Gt 5 | | | |
| Clear coat I unstabilized/ clear coat II stabilized with 3% Tinuvin 109/ 1.5% Tinuvin 400 | Gt 0 | Gt 5 | | |

TABLE 4-continued

Adhesion of clear coats on electrocoats after weathering

| Sample | Cross hatch value (ISO 2409 after ... hours |  |  |  |
|---|---|---|---|---|
|  | 250 h | 1000 h | 1500 h | 2000 h |
| Clear coat I stabilized with 3% compound 1B | Gt 0 | Gt 0 | Gt 0 | Gt 1 |
| Clear coat II stabilized with 3% Tinuvin 109/ 1.5% Tinuvin 400 |  |  |  |  |

Note:
Gt 0 according to ISO 2409 = best (no los of adhesion)
Gt 5 = worst (complete delamination)

Example B5

Photo Permanence of UV-Absorbers

Experimental parameters are as outlined in Example B 1 with the exception that the UV-absorbers are tested in combination with HALS as co-stabilizer, i.e. 1% TINUVIN® 123 based on the solids content of the formulation.

TABLE 5 photo permanence of UV-absorbers during Xe—WOM exposure

| Compound | % UV-absorber retained after ... hours Xe—WOM exposure |  |  |  |  |
|---|---|---|---|---|---|
|  | 1000 | 1500 | 2000 | 3000 | 4000 h |
| 1b | 98.0 | 92.4 | 89.8 |  |  |
| 3d (I) | 92.9 | 88.3 | 83.2 |  |  |
| 3d (II) | 87.8 | 80.3 | 72.9 |  |  |
| 3d (III) | 92.8 | 85.8 | 83.4 |  |  |
| 3d (IV) | 97.9 | 91.4 | 88.5 |  |  |
| 3d (V) | 98.0 | 86.1 | 80.9 |  |  |

Example B6

Subsequent Clear Coats

In a further example two subsequent clear coats are applied on top of each other. The first clear coat (Clear coat 1) is stabilized with the UV absorbers of the present invention together with a sterically hindered amine and applied as described in Example B 1. A second thermosetting acryl/melamine clear coat (based on Viacryl® SC 303/Viacryl® SC 370/Maprenal® MF 650) is subsequently sprayed onto the first clear coat resulting in a dry film thickness of the second clear coat (clear coat ii) of 40 µm after cure (130° C./30'). The second clear coat is stabilized with a UV-absorber combination of 3% Tinuvin® 109/1.5% Tinuvin 400® and 1% Tinuvin 152® as co-stabilizer (HALS). Reference is the unstabilized first clear coat.

As described in example B1, the UV-transmission spectra are recorded prior to exposure of the specimens using a UV/VIS spectrometer (Perkin Elmer, Lamda 40). Subsequently the specimens are exposed in a Xenon-WOM wetherometer (Atlas Corp.) according to SAE J 1960. The transmission values (determined at 396 nm) as a function of the exposure period are monitored by recording the transmission spectra after regular exposure intervals. The test results are summarized in Table 6:

TABLE 6 transmission values (determined at 396 nm) after specific exposure intervals during Xe—WOM exposure

| UV-absorbers | transmission values (%) after ... hours |  |  |  |  |
|---|---|---|---|---|---|
|  | Initial | 1000 | 2000 | 3000 | 4000 |
| Clear coat I: unstabilized Clear coat II: 3% Tinuvin ® 109/ 1.5% Tinuvin ® 400 | 21.3 | 24.3 | 25.4 | 26.4 | 28.1 |
| Clear coat I: 3% 3d (I) Clear coat II: 3% Tinuvin ® 109/ 1.5% Tinuvin ® 400 | 0.62 | 0.67 | 0.77 |  |  |
| Clear coat I: 3% 3d (II) Clear coat II: 3% Tinuvin ® 109/ 1.5% Tinuvin ® 400 | 0.50 | 0.59 | 0.76 |  |  |
| Clear coat I: 3% 3d (III) Clear coat II: 3% Tinuvin ® 109/ 1.5% Tinuvin ® 400 | 1.06 | 1.17 | 1.31 |  |  |
| Clear coat I: 3% 3d (IV) Clear coat II: 3% Tinuvin ® 109/ 1.5% Tinuvin ® 400 | 1.41 | 1.45 | 1.58 |  |  |
| Clear coat I: 3% 3d (V) Clear coat II: 3% Tinuvin ® 109/ 1.5% Tinuvin ® 400 | 1.31 | 1.35 | 1.46 |  |  |

| Clearcoat II formulation: |  |
|---|---|
| a) Viacryl ® SC 303[1] (65% solution in xylene/butanol, 26:9 wt./wt.) | 27.51 g |
| b) Viacryl ® SC 370[2] (75% in Solvesso 100[3]) | 23.34 g |
| c) Maprenal ® MF 650[4] (55% in isobutanol) | 27.29 g |
| d) Butylacaetate/butanol (37:8 wt./wt.) | 4.33 g |
| e) Isobutanol | 4.87 g |
| f) Solvesso ® 150[5] | 2.72 g |
| g) Crystal oil 30[6] | 8.74 g |
| h) Baysilone ® MA[7] (1% in Solvesso 150) | 1.20 g |
| Total | 100.00 g |

The invention claimed is:

1. A compound of formulae (I) or (II)

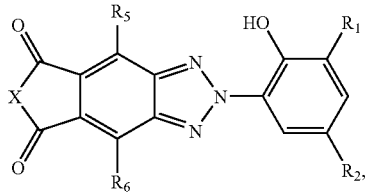 (I)

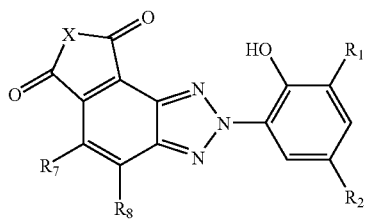 (II)

wherein $R_1$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $R_1$ is a group

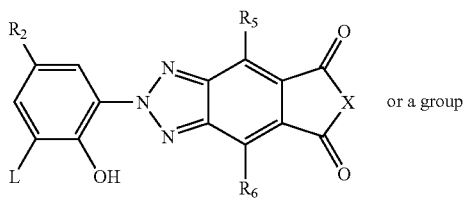 or a group

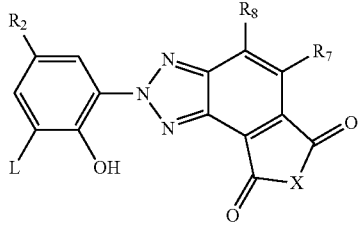

wherein L is alkylene of 1 to 12 carbon atoms, alkylidene of 2 to 12 carbon atoms, benzylidene, p-xylylene or cycloalkylene of 5 to 7 carbon atoms $R_2$ is straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms phenyl, or said phenyl or said phenylalkyl substituted on the phenyl ring by 1 to 3 alkyl of 1 to 4 carbon atoms; or said alkyl substituted by one or more —OH, —OCO—$R_{11}$, —O$R_{14}$, —NCO or —NH$_2$ groups or mixtures thereof, or said alkyl or said alkenyl interrupted by one or more —O—, —NH— or N$R_{14}$— groups or mixtures thereof and which can be unsubstituted or substituted by one or more —OH, —O$R_{14}$ or —NH$_2$ groups or mixtures thereof; where $R_{11}$ is hydrogen, straight or branched chain $C_1$-$C_{18}$alkyl, $C_5$-$C_{12}$cycloalkyl, straight or branched chain $C_3$-$C_8$alkenyl, phenyl, naphthyl or $C_7$-$C_{15}$-phenylalkyl; and $R_{14}$ is hydrogen, straight or branched chain alkyl of 1 to 24 carbon atoms; or $R_2$ is —O$R_{14}$, a group —C(O)—O—$R_{14}$, —C(O)—NH$R_{14}$ or —C(O)—N$R_{14}$R'$_{14}$ wherein R'$_{14}$ has the same meaning as $R_{14}$; or $R_2$ is —S$R_{13}$, —NH$R_{13}$ or —N($R_{13}$)$_2$; or $R_2$ is (CH$_2$)$_m$CO—X$_1$—(Z)$_p$—Y—$R_{15}$ wherein X$_1$ is —O— or —N($R_{16}$)—, Y is —O— or —N($R_{17}$)— or a direct bond, Z is $C_2$-$C_{12}$-alkylene, $C_4$-$C_{12}$alkylene interrupted by one to three nitrogen atoms, oxygen atoms or a mixture thereof, or is $C_3$-$C_{12}$alkylene, butenylene, butynylene, cyclohexylene or phenylene, each of which may be additionally substituted by a hydroxyl group;

or a group

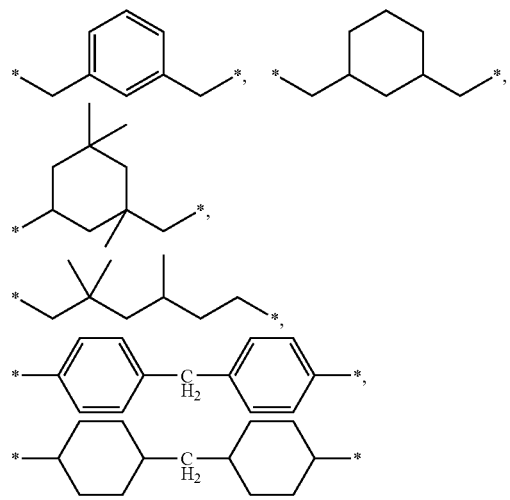

wherein * denotes a bond or when Y is a direct bond, Z can additionally also be a direct bond;

m is zero, 1 or 2, p is 1, or p is also zero when X and Y are —N($R_{16}$)— and —N($R_{17}$)—, respectively, $R_{15}$ is hydrogen, $C_1$-$C_{12}$alkyl, a group

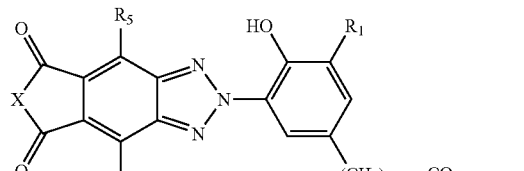 or

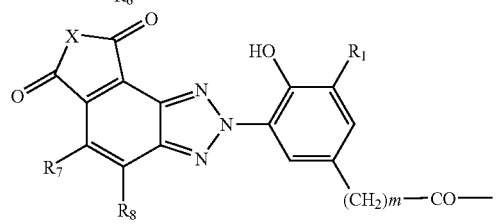

or a group —CO—C($R_{18}$)=C(H)$R_{19}$ or, when Y is —N($R_{17}$)—, forms together with $R_1$—, a group —CO—CH=CH—CO— wherein $R_{18}$ is hydrogen or methyl, and $R_{19}$ is hydrogen, methyl or —CO—$X_1$—$R_{20}$, wherein $R_{20}$ is hydrogen, $C_1$-$C_{12}$alkyl or a group of formulae

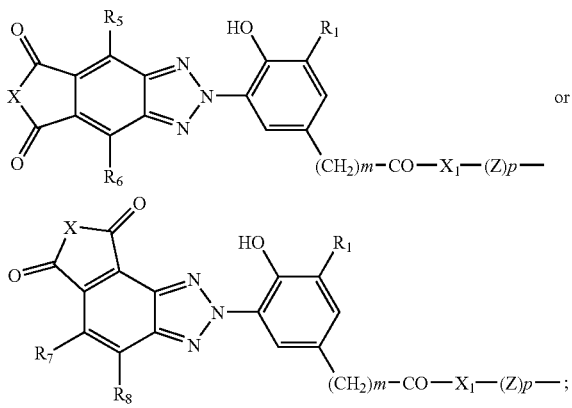

$R_5$, $R_6$, $R_7$ and $R_8$ are independently hydrogen, halogen, CN, $NO_2$ or $NH_2$;

$R_{13}$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, phenyl or naphthyl, which both may be substituted by one or two alkyl of 1 to 4 carbon atoms;

$R_{16}$ and $R_{17}$ independently of one another are hydrogen, $C_1$-$C_{12}$-alkyl, $C_3$-$C_{12}$-alkyl interrupted by 1 to 3 oxygen atoms, or is cyclohexyl or $C_7$-$C_{15}$phenylalkyl, and $R_{16}$ together with $R_{17}$ in the case where Z is ethylene, also forms ethylene;

X is O or $NE_1$ wherein $E_1$ is hydrogen, straight or branched chain $C_1$-$C_{24}$alkyl, straight or branched chain $C_2$-$C_{18}$alkenyl, $C_2$-$C_6$alkylnyl, $C_5$-$C_{12}$cycloalkyl, phenyl, naphthyl or $C_7$-$C_{15}$phenylalkyl; or said straight or branched chain $C_1$-$C_{24}$alkyl, straight or branched chain $C_2$-$C_{24}$alkenyl, $C_5$-$C_{12}$ cycloalkyl, $C_2$-$C_6$ alkinyl can be substituted by one or more —F, —OH, —$OR_{22}$, —$NH_2$, —$NHR_{22}$, —$N(R_{22})_2$, —$NHCOR_{23}$, —$NR_{22}COR_{23}$, —$OCOR_{24}$, —$COR_{25}$, —$SO_2R_{26}$, —$PO(R_{27})_n(R_{28})_{2-n}$, —$Si(R_{29})_n(R_{30})_{3-n}$, —$Si(R_{22})_3$, —$N^+(R_{22})_3$ $A^-$, —$S^+(R_{22})_2$ $A^-$, -oxiranyl groups or mixtures thereof; said straight or branched chain $C_1$-$C_{24}$ alkyl, straight or branched chain unsubstituted or substituted $C_2$-$C_{24}$ alkenyl, $C_5$-$C_{12}$ cycloalkyl or $C_2$-$C_6$ alkinyl can also be interrupted by one or more —O—, —S—, —NH— or —$NR_{22}$— groups or combinations thereof;

said phenyl, naphthyl or $C_7$-$C_{15}$phenylalkyl can also be substituted by one or more -halogen, —CN, —$CF_3$, —$NO_2$, —$NHR_{22}$, —$N(R_{22})_2$, —$SO_2R_{26}$, —$PO(R_{27})_n(R_{28})_2$, —OH, —$OR_{22}$, —$COR_{25}$, —$R_{25}$; wherein n is 0, 1 or 2;

$R_{22}$ is straight or branched chain $C_1$-$C_{18}$ alkyl, straight or branched chain $C_2$-$C_{18}$ alkenyl, $C_5$-$C_{10}$ cycloalkyl, phenyl or naphthyl, $C_7$-$C_{15}$ phenylalkyl, or two $R_{22}$ when attached to an N or Si atom can form together with the atom to which they are bonded a pyrrolidine, piperidine or morpholine ring;

$R_{23}$ is hydrogen, $OR_{22}$, $NHR_{22}$, $N(R_{22})_2$ or has the same meaning as $R_{22}$, $R_{24}$ is $OR_{22}$, $NHR_{22}$, $N(R_{22})_2$ or has the same meaning as $R_{22}$, $R_{25}$ is hydrogen, OH, $OR_{22}$, $NHR_{22}$ or $N(R_{22})_2$, O-glycidyl or has the same meaning as $R_{22}$, $R_{26}$ is OH, $OR_{22}$, $NHR_{22}$ or $N(R_{22})_2$, $R_{27}$ is $NH_2$, $NHR_{22}$ or $N(R_{22})_2$, $R_{28}$ is OH or $OR_{22}$, $R_{29}$ is Cl or $OR_{22}$, $R_{30}$ is straight or branched chain $C_1$-$C_{18}$ alkyl; or $E_1$ is a group

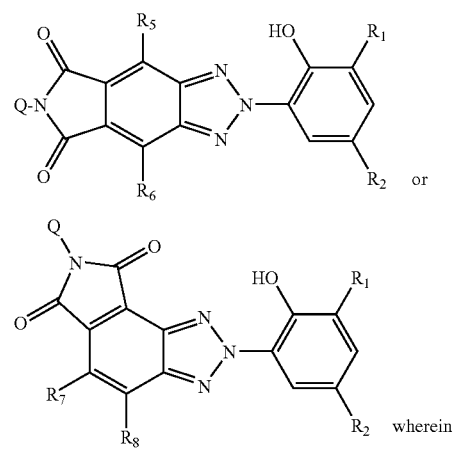

$R_1$ to $R_8$ have the meanings as defined above and

Q is straight or branched $C_2$-$C_{12}$alkylene, $C_2$-$C_{12}$alkylene, which is interrupted by one or more —O—, NH or $NR_{14}$ atoms, $C_5$-$C_{10}$cycloalkylene, para-phenylene or a group

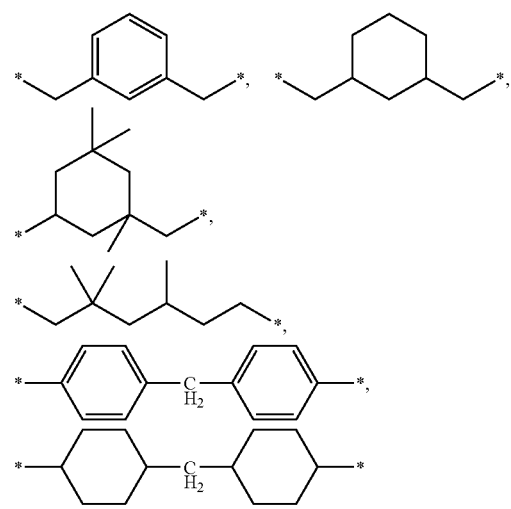

wherein * denotes a bond.

2. A compound according to claim 1 of formulae (I) or (II) wherein $R_1$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $R_1$ is a group

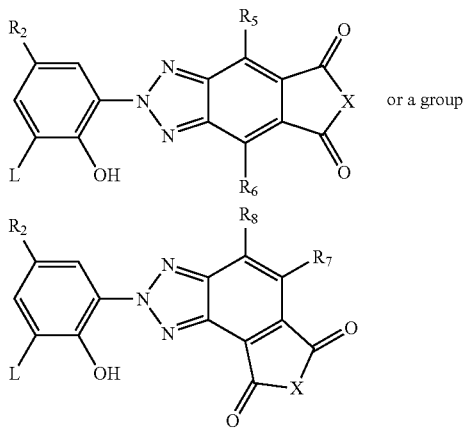 or a group wherein L is alkylene of 1 to 12 carbon atoms, alkylidene of 2 to 12 carbon atoms, benzylidene, p-xylylene or cycloalkylene of 5 to 7 carbon atoms;

$R_2$ is straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms phenyl, or said phenyl or said phenylalkyl substituted on the phenyl ring by 1 to 3 alkyl of 1 to 4 carbon atoms; or $R_2$ is —$(CH_2)_m$—CO—$X_1$—$(Z)_p$—Y—$R_{15}$ wherein
$X_1$ is —O—,
Y is —O— or a direct bond,
Z is $C_2$-$C_{12}$-alkylene, $C_4$-$C_{12}$alkylene interrupted by one to three nitrogen atoms, oxygen atoms or a mixture thereof, or when Y is a direct bond, Z can additionally also be a direct bond;
m is 2,
p is 1,
$R_{15}$ is hydrogen, $C_1$-$C_{12}$alkyl or a group

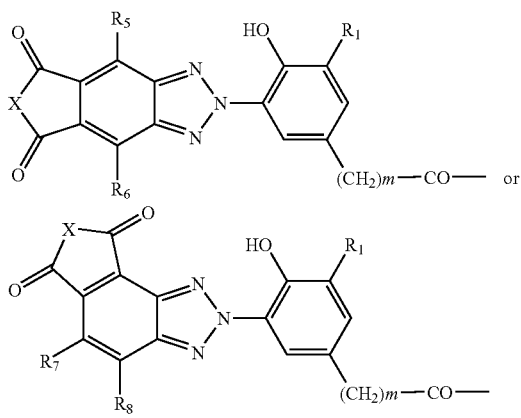

$R_5$, $R_6$, $R_7$ and $R_8$ are independently hydrogen, Cl or Br;
X is O or $NE_1$ wherein
$E_1$ is hydrogen, straight or branched chain $C_1$-$C_{24}$alkyl, straight or branched chain $C_2$-$C_{18}$alkenyl, $C_2$-$C_6$alkylnyl, $C_5$-$C_{12}$cycloalkyl, phenyl, naphthyl or $C_7$-$C_{15}$phenylalkyl; or said straight or branched chain $C_1$-$C_{24}$alkyl, straight or branched chain $C_2$-$C_{24}$alkenyl, $C_5$-$C_{12}$ cycloalkyl, $C_2$-$C_6$ alkinyl can be substituted by one or more —F, —OH, —$OR_{22}$, —$NH_2$, —$NHR_{22}$, —$N(R_{22})_2$, —$NHCOR_{23}$, —$NR_{22}COR_{23}$, —$OCOR_{24}$, —$COR_{25}$, —$SO_2R_{26}$, —$PO(R_{27})_n(R_{28})_{2-n}$, —$Si(R_{29})_n(R_{30})_{3-n}$, —$Si(R_{22})_3$, —$N^+(R_{22})_3$ $A^-$, —$S^+(R_{22})_2$ $A^-$, -oxiranyl groups or mixtures thereof; said straight or branched chain $C_1$-$C_{24}$alkyl, straight or branched chain unsubstituted or substituted $C_2$-$C_{24}$ alkenyl, $C_5$-$C_{12}$ cycloalkyl or $C_2$-$C_6$ alkinyl can also be interrupted by one or more —O—, —S—, —NH— or —$NR_{22}$— groups or combinations thereof;

said phenyl, naphthyl or $C_7$-$C_{15}$phenylalkyl can also be substituted by one or more -halogen, —CN, —$CF_3$, —$NO_2$, —$NHR_{22}$, —$N(R_{22})_2$, —$SO_2R_{26}$, —$PO(R_{27})_n(R_{28})_{2-n}$, —OH, —$OR_{22}$, —$COR_{25}$, —$R_{25}$; wherein
n is 0, 1 or 2;

$R_{22}$ is straight or branched chain $C_1$-$C_{18}$ alkyl, straight or branched chain $C_2$-$C_{18}$ alkenyl, $C_5$-$C_{10}$cycloalkyl, phenyl or naphthyl, $C_7$-$C_{15}$ phenylalkyl, or two $R_{22}$ when attached to an N or Si atom can form together with the atom to which they are bonded a pyrrolidine, piperidine or morpholine ring;

$R_{23}$ is hydrogen, $OR_{22}$, $NHR_{22}$, $N(R_{22})_2$ or has the same meaning as $R_{22}$,
$R_{24}$ is $OR_{22}$, $NHR_{22}$, $N(R_{22})_2$ or has the same meaning as $R_{22}$,
$R_{25}$ is hydrogen, OH, $OR_{22}$, $NHR_{22}$ or $N(R_{22})_2$, O-glycidyl or has the same meaning as $R_{22}$,
$R_{26}$ is OH, $OR_{22}$, $NHR_{22}$ or $N(R_{22})_2$,
$R_{27}$ is $NH_2$, $NHR_{22}$ or $N(R_{22})_2$,
$R_{28}$ is OH or $OR_{22}$,
$R_{29}$ is Cl or $OR_{22}$,
$R_{30}$ is straight or branched chain $C_1$-$C_{18}$alkyl; or

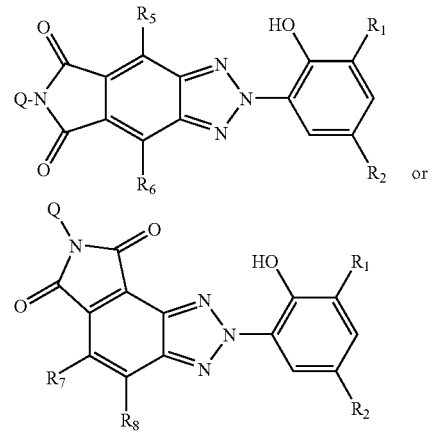

$E_1$ is a group wherein
$R_1$ to $R_8$ have the meanings as defined above and
Q is straight or branched $C_2$-$C_{12}$alkylene, $C_5$-$C_{10}$cycloalkylene or para-phenylene or a group,

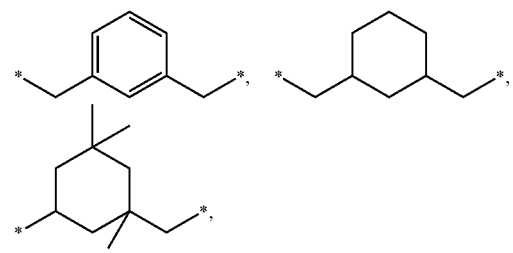

-continued

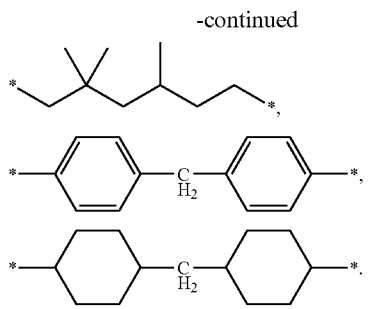

3. A compound according to claim 2 wherein $R_1$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms $R_2$ is straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms phenyl, or said phenyl or said phenylalkyl substituted on the phenyl ring by 1 to 3 alkyl of 1 to 4 carbon atoms; or $R_2$ is $-(CH_2)_2-CO-O-(Z)-O-R_{15}$ wherein Z is $C_2$-$C_{12}$-alkylene, $C_4$-$C_{12}$alkylene interrupted by one to three oxygen atoms;

$R_{15}$ is hydrogen, $C_1$-$C_{12}$alkyl or a group

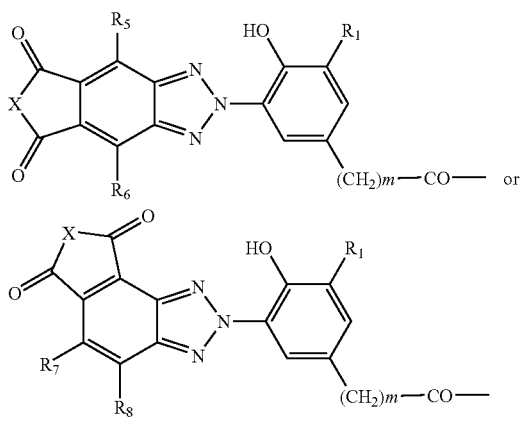

$R_5$, $R_6$, $R_7$ and $R_8$ are independently hydrogen, Cl or Br;

X is O or $NE_1$ wherein $E_1$ is hydrogen, straight or branched chain $C_1$-$C_{24}$alkyl, $C_5$-$C_{12}$cycloalkyl, phenyl or $C_7$-$C_{15}$phenylalkyl;

or said straight or branched chain $C_1$-$C_{24}$alkyl or $C_5$-$C_{12}$ cycloalkyl can be substituted by one or more —F, —OH, —$OR_{22}$, —$NH_2$, —$NHR_{22}$, —$N(R_{22})_2$;

said phenyl or $C_7$-$C_{15}$phenylalkyl can also be substituted by one or more -halogen, —ON, —$OF_3$, —OH, —$OR_{22}$, —$COR_{22}$, —$R_{22}$; wherein $R_{22}$ is straight or branched chain $C_1$-$C_{18}$ alkyl, straight or branched chain $C_2$-$C_{18}$ alkenyl, $C_5$-$C_{10}$ cycloalkyl, $C_6$-$C_{16}$phenyl or naphthyl, $C_7$-$C_{15}$ phenylalkyl; or $E_1$ is a group

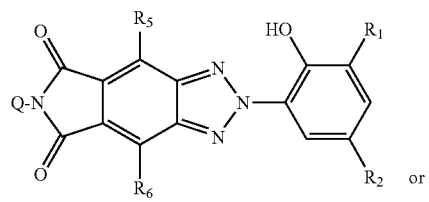

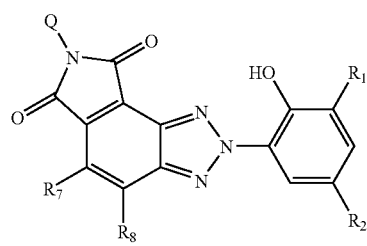

wherein $R_1$ to $R_8$ have the meanings as defined above and

Q is $C_2$-$C_{12}$alkylene, $C_5$-$C_7$cycloalkylene, para-phenylene or a group

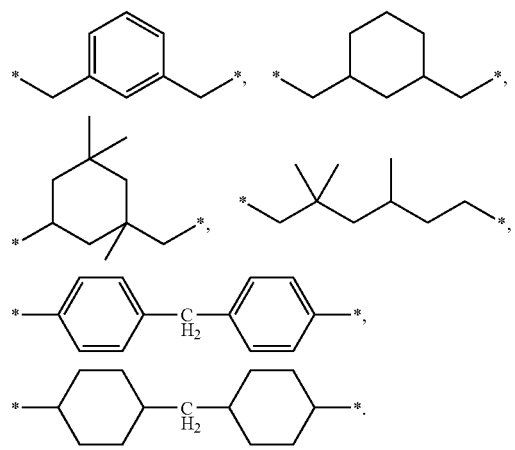

4. A compound according to claim 3 wherein $R_1$ is hydrogen, straight or branched chain alkyl of 1 to 12 carbon atoms or phenylalkyl of 7 to 15 carbon atoms;

$R_2$ is straight or branched chain alkyl of 1 to 12 carbon atoms or phenylalkyl of 7 to 15 carbon atoms, phenyl, or said phenyl or said phenylalkyl substituted on the phenyl ring by 1 to 3 alkyl of 1 to 4 carbon atoms;

$R_5$ and $R_6$ are hydrogen or one of both is Cl or Br;

$R_7$ and $R_8$ are independently hydrogen, Cl or Br;

X is O or $NE_1$ wherein $E_1$ is hydrogen, straight or branched chain $C_1$-$C_6$alkyl, which is unsubstituted or substituted by 1 to 4 OH, phenyl, which is unsubstituted or substituted by F, $CF_3$, CN or Cl, or $C_7$-$C_9$phenylalkyl.

5. A compound according to claim 1 of formula (I).

6. A compound according to claim 1, which is

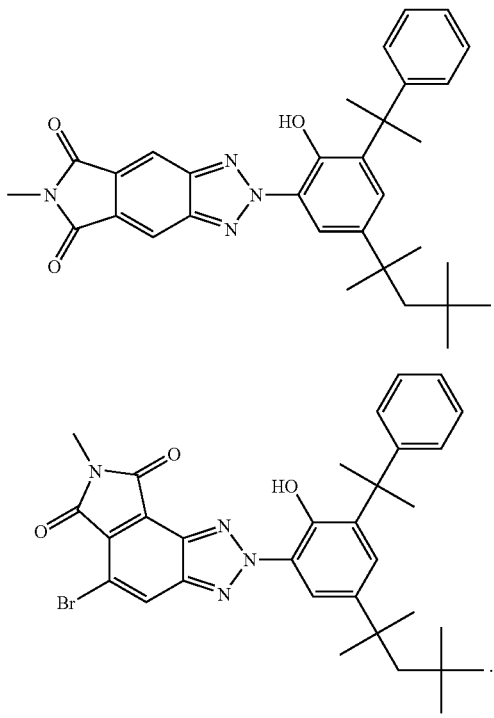

(1b)

or (2c)

7. A process for the preparation of a compound of formulae (I) or (II)

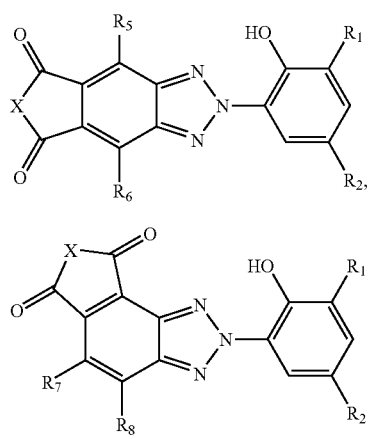

(I)

(II)

wherein $R_1$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $R_1$ is a group

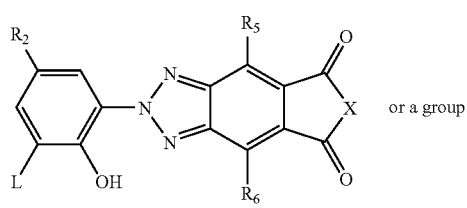

or a group

-continued

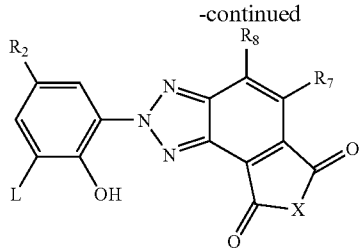

wherein L is alkylene of 1 to 12 carbon atoms, alkylidene of 2 to 12 carbon atoms, benzylidene, p-xylylene or cycloalkylene of 5 to 7 carbon atoms;

$R_2$ is straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or said alkyl substituted by one or more —OH, —OCO—$R_{11}$, —$OR_{14}$, —NCO or —$NH_2$ groups or mixtures thereof, or said alkyl or said alkenyl interrupted by one or more —O—, —NH— or —$NR_{14}$— groups or mixtures thereof and which can be unsubstituted or substituted by one or more —OH, —$OR_{14}$ or —$NH_2$ groups or mixtures thereof; where $R_{11}$ is hydrogen, straight or branched chain $C_1$-$C_{18}$alkyl, $C_5$-$C_{12}$cycloalkyl, straight or branched chain $C_3$-$C_8$alkenyl, phenyl, naphthyl or $C_7$-$C_{15}$phenylalkyl; and $R_{14}$ is hydrogen, straight or branched chain alkyl of 1 to 24 carbon atoms; or $R_2$ is —$OR_{14}$, a group —C(O)—O—$R_{14}$, —C(O)—$NHR_{14}$ or —C(O)—$NR_{14}R'_{14}$ wherein $R'_{14}$ has the same meaning as $R_{14}$; or $R_2$ is —$SR_{13}$, —$NHR_{13}$ or —$N(R_{13})_2$; or $R_2$ is —$(CH_2)_mCO$—$X_1$—$(Z)_p Y$—$R_{15}$ wherein $X_1$ is —O— or —$N(R_{16})$—, Y is —O— or —$N(R_{17})$— or a direct bond, Z is $C_2$-$C_{12}$-alkylene, $C_4$-$C_{12}$alkylene interrupted by one to three nitrogen atoms, oxygen atoms or a mixture thereof, or is $C_3$-$C_{12}$alkylene, butenylene, butynylene, cyclohexylene or phenylene, each of which may be additionally substituted by a hydroxyl group;

or a group

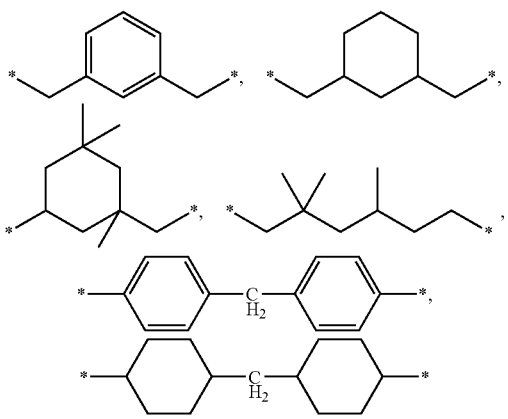

wherein * denotes a bond or when Y is a direct bond, Z can additionally also be a direct bond;

m is zero, 1 or 2, p is 1, or p is also zero when X and Y are —N($R_{16}$)— and —N($R_{17}$)—, respectively, $R_{15}$ is hydrogen, $C_1$-$C_{12}$alkyl, a group

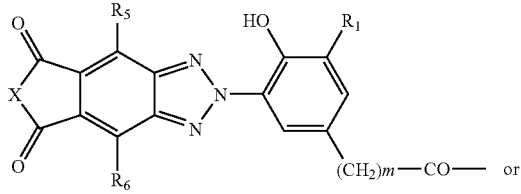

or a group —CO—C($R_{18}$)C(H)$R_{19}$ or, when Y is —N($R_{17}$)—, forms together with $R_{17}$ a group —CO—CH=CH—CO— wherein $R_{18}$ is hydrogen or methyl, and $R_{19}$ is hydrogen, methyl or —CO—$X_1$—$R_{20}$, wherein $R_{20}$ is hydrogen, $C_1$-$C_{12}$alkyl or a group of formulae

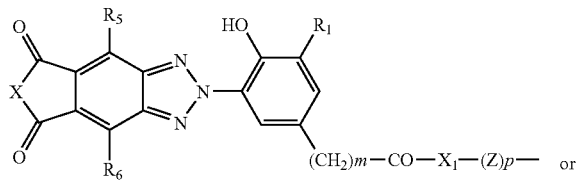

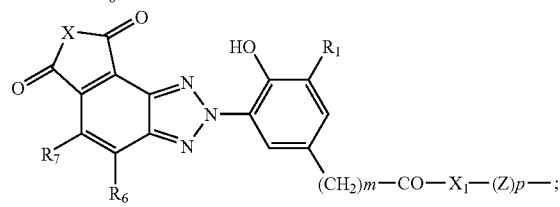

$R_5$, $R_6$, $R_7$ and $R_8$ are independently hydrogen, halogen, CN, $NO_2$ or $NH_2$;

$R_{13}$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, phenyl or naphthyl, which both may be substituted by one or two alkyl of 1 to 4 carbon atoms;

$R_{16}$ and $R_{17}$ independently of one another are hydrogen, $C_1$-$C_{12}$-alkyl, $C_3$-$C_{12}$-alkyl interrupted by 1 to 3 oxygen atoms, or is cyclohexyl or $C_7$-$C_{15}$phenylalkyl, and $R_{16}$ together with $R_{17}$ in the case where Z is ethylene, also forms ethylene;

X is O or $NE_1$ wherein $E_1$ is hydrogen, straight or branched chain $C_1$-$C_{24}$alkyl, straight or branched chain $C_2$-$C_{18}$alkenyl, $C_2$-$C_6$alkylnyl, $C_5$-$C_{12}$cycloalkyl, phenyl, naphthyl or $C_7$-$C_{15}$phenylalkyl; or said straight or branched chain $C_1$-$C_{24}$ alkyl, straight or branched chain $C_2$-$C_{24}$ alkenyl, $C_5$-$C_{12}$ cycloalkyl, $C_2$-$C_6$ alkinyl can be substituted by one or more —F, —OH, —$OR_{22}$, —$NH_2$, —$NHR_{22}$, —$N(R_{22})_2$, —$NHCOR_{23}$, —$NR_{22}COR_{23}$, —$OCOR_{24}$, —$COR_{25}$, —$SO_2R_{26}$, —$PO(R_{27})_n(R_{28})_{2-n}$, —$Si(R_{29})_n$ ($R_{30})_{3-n}$, $Si(R_{22})_3$, —$N^+(R_{22})_3$ $A^-$, —$S^+(R_{22})_2A^-$, -oxiranyl groups or mixtures thereof; said straight or branched chain $C_1$-$C_{24}$ alkyl, straight or branched chain unsubstituted or substituted $C_2$-$C_{24}$ alkenyl, $C_5$-$C_{12}$ cycloalkyl or $C_2$-$C_6$ alkinyl can also be interrupted by one or more —O—, —S—, —NH— or —$NR_{22}$— groups or combinations thereof;

said phenyl, naphthyl or $C_7$-$C_{15}$phenylalkyl can also be substituted by one or more -halogen, —CN, —$CF_3$, —$NO_2$, —$NHR_{22}$, —$N(R_{22})_2$, —$SO_2R_{26}$, —$PO(R_{27})_n(R_2)_{2-n}$, —OH, —$OR_{22}$, —$COR_{25}$, —$R_{25}$;

wherein n is 0, 1 or 2;

$R_{22}$ is straight or branched chain $C_1$-$C_{18}$ alkyl, straight or branched chain $C_2$-$C_{18}$ alkenyl, $C_5$-$C_{10}$ cycloalkyl, phenyl or naphthyl, $C_7$-$C_{15}$ phenylalkyl, or two $R_{22}$ when attached to an N or Si atom can form together with the atom to which they are bonded a pyrrolidine, piperidine or morpholine ring;

$R_{23}$ is hydrogen, $OR_{22}$, $NHR_{22}$, $N(R_{22})_2$ or has the same meaning as $R_{22}$, $R_{24}$ is $OR_{22}$, $NHR_{22}$, $N(R_{22})_2$ or has the same meaning as $R_{22}$, $R_{25}$ is hydrogen, OH, $OR_{22}$, $NHR_{22}$ or $N(R_{22})_2$, O-glycidyl or has the same meaning as $R_{22}$, $R_{26}$ is OH, $OR_{22}$, $NHR_{22}$ or $N(R_{22})_2$, $R_{27}$ is $NH_2$, $NHR_{22}$ or $N(R_{22})_2$, $R_{28}$ is OH or $OR_{22}$, $R_{29}$ is Cl or $OR_{22}$, $R_{30}$ is straight or branched chain $C_1$-$C_{18}$ alkyl; or $E_1$ is a group

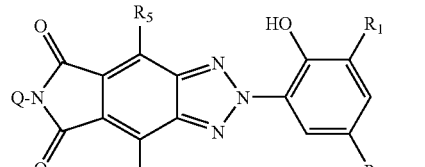

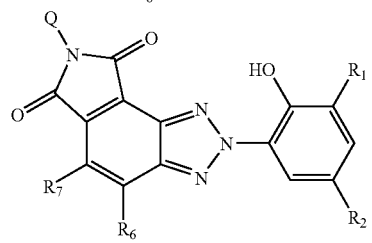

wherein $R_1$ to $R_5$ have the meanings as defined above and

Q is straight or branched $C_2$-$C_{12}$alkylene, $C_2$-$C_{12}$alkylene, which is interrupted by one or more O—, NH or $NR_{14}$ atoms, $C_5$-$C_{10}$cycloalkylene, para-phenylene or a group

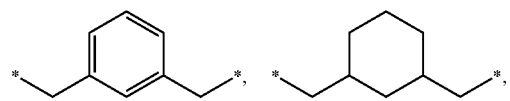

-continued

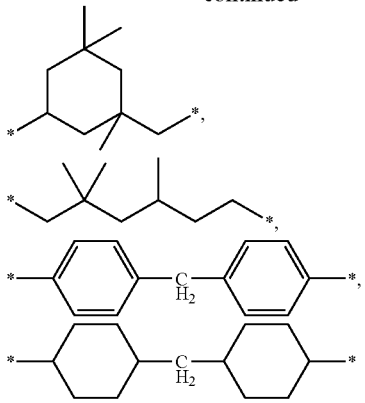

wherein * bond, which process comprises reacting a compound of formulae (III), (IV) or (V)

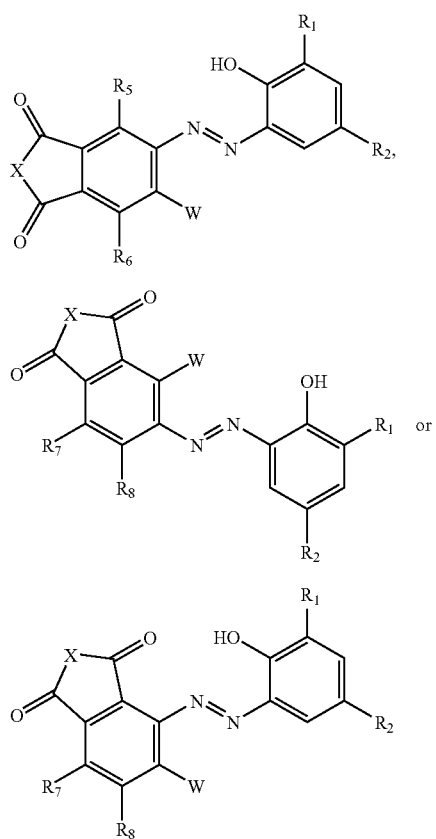

wherein W is halogen or nitro
with an azide compound of formula (X)

$$M^{n+}(N_3^-)_r$$ (X)

wherein

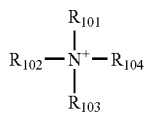

M is an n-valent metal cation, or
$R_{101}$, $R_{102}$, $R_{103}$ and $R_{104}$ are each independently of the others hydrogen or $C_1$-$C_{18}$alkyl,
$R_{105}$ is $C_1$-$C_{18}$alkyl, and
r is 1, 2 or 3.

8. A process according to claim 7 wherein the reaction is carried out in a solvent.

9. A process according to claim 7 wherein the molar ratio of the amount of compound of formula (III), (IV) or (V) to the amount of azide compound of formula (X) is from 1:1 to 1:3.

10. A process according to claim 7, wherein the reaction is carried out in the presence of a catalyst.

11. A composition stabilized against light-induced degradation which comprises,
   (a) an organic material subject to light-induced degradation, and
   (b) a compound of formula (I) or (II) according to claim 1.

12. A composition according to claim 11 which contains additionally a sterically hindered amine stabilizer and/or a UV absorber selected from the group consisting of the s-triazines, the oxanilides, the hydroxybenzophenones, benzoates, the α-cyanoacrylates and the benzotriazoles different from those of formulae (I) or (II).

13. A composition according to claim 11 wherein the organic material is a recording material.

14. A composition according to claim 11 wherein the organic material is a natural, semi-synthetic or synthetic polymer.

15. A composition according to claim 14 wherein the polymer is a thermoplastic polymer.

16. A composition according to claim 11 wherein the organic material is a coating.

17. A composition according to claim 16 wherein the coating is an automotive coating.

18. A composition according to claim 16 wherein the coating is applied over a substrate, which is sensitive to electromagnetic radiation of wavelengths greater than 380 nm.

19. A composition according to claim 11, wherein the compound of formula (I) or (II) is present in an amount of from 0.1% to 30% by weight, based on the weight of the organic material.

* * * * *